United States Patent
Hiatt et al.

(10) Patent No.: US 6,696,620 B2
(45) Date of Patent: Feb. 24, 2004

(54) IMMUNOGLOBULIN BINDING PROTEIN ARRAYS IN EUKARYOTIC CELLS

(75) Inventors: Andrew C. Hiatt, San Diego, CA (US); Mich B. Hein, Fallbrook, CA (US)

(73) Assignee: Epicyte Pharmaceutical, Inc., San Diego, CA (US)

( * ) Notice: Subject to any disclaimer, the term of this patent is extended or adjusted under 35 U.S.C. 154(b) by 0 days.

(21) Appl. No.: 09/563,222

(22) Filed: May 2, 2000

(65) Prior Publication Data

US 2003/0079253 A1 Apr. 24, 2003

(51) Int. Cl.$^7$ ............................................. C12N 15/00
(52) U.S. Cl. ....................... 800/288; 800/294; 800/281; 800/278; 435/69.1; 435/320.1; 435/219; 435/DIG. 47; 435/DIG. 49
(58) Field of Search ................................ 800/294, 288, 800/281, 278; 435/69.1, 320.1, 219, DIG. 47, DIG. 49

(56) References Cited

U.S. PATENT DOCUMENTS

| | | | |
|---|---|---|---|
| 4,762,785 A | 8/1988 | Comai | 435/172.3 |
| 4,771,002 A | 9/1988 | Gelvin | 435/172.3 |
| 4,816,397 A | 3/1989 | Boss et al. | 435/68 |
| 4,816,567 A | 3/1989 | Cabilly et al. | 530/387 |
| 4,837,167 A | 6/1989 | Schoemaker et al. | 436/513 |
| 4,956,282 A | 9/1990 | Goodman et al. | 435/69.51 |
| 5,169,933 A | 12/1992 | Anderson et al. | 530/391.3 |
| 5,202,422 A | 4/1993 | Hiatt et al. | 530/387.3 |
| 5,240,833 A | 8/1993 | Nudelman et al. | 435/70.21 |
| 5,284,746 A | 2/1994 | Springer et al. | 424/85.8 |
| 5,484,707 A | 1/1996 | Goldblum et al. | 435/7.91 |
| 5,512,443 A | 4/1996 | Schlom et al. | 435/7.23 |
| 5,639,947 A | 6/1997 | Hiatt et al. | 800/205 |
| 5,731,168 A | 3/1998 | Carter et al. | 435/69.1 |
| 5,840,526 A | 11/1998 | Casterman et al. | 435/69.1 |
| 5,959,177 A | 9/1999 | Hein et al. | 800/288 |
| 6,045,774 A | 4/2000 | Hiatt et al. | 424/9.1 |

FOREIGN PATENT DOCUMENTS

| | | |
|---|---|---|
| EP | 0732404 A1 | 9/1996 |
| WO | WO 87/00865 | 2/1987 |
| WO | WO 88/04936 | 7/1988 |
| WO | WO 94/04678 | 3/1994 |
| WO | WO 98/30591 | 7/1998 |
| WO | WO 98/30592 | 7/1998 |
| WO | WO 99/28502 | 6/1999 |

OTHER PUBLICATIONS

Aizpurua and Russell–Jones, "Oral Vaccination: Identification of Classes of Proteins that Provoke an Immune Response upon Oral Feeding" *J. Exp. Med., 167*:440–451, 1988.

Brandtzaeg and Baklien, "Immunohistochemical Studies of the Immunoglobulin–Producing Cell Systems of the Human Intestinal Mucosa," *Acta histochemica S. 21*:105–119, 1980.

Brandtzaeg and Prydz, "Direct Evidence for an Integrated Function of J Chain and Secretory Component in Epithelial Transport of Immunoglobulins," *Nature* 311: 71–73 1984.

Brown and Koshland, "Evidence for a Long–Range Conformational Change Induced by Antigen Binding to IgM Antibody," *Proc. Natl. Acad. Sci. USA* 74(12): 5682–5686, 1977.

Burns et al., "Protective Effect of Rotavirus VP6–Specific IgA Monoclonal Antibodies that Lack Neutralizing Activity," *Science* 272:104–107, 1996.

Carayannopoulos et al., "Recombinant Human IgA Expressed in Insect Cells", *Proc. Natl. Acad. Sci. USA, 91*:8348–8352 (1994).

Carayannopoulos et al., "Localization of the Binding Site for the Nonocyte Immunoglobulin (Ig) A–Fc Receptor (CD89) to the Domain Boundary Between $C\alpha 2$ and $C\alpha 3$ in Human IgA1," *J. Exp. Med. 183*: 1579–1586, 1986.

Chrispeels, "Sorting of Proteins in the Secretory System" *Ann. Rev. Plant. Physiol. Plant Mol. Biol. 42*: 21–53 (1991).

Creighton, Thomas E., *Proteins Structures and Molecular Principles*, W.H. Freeman and Company, New York, pp. 2, 86–87, 1984.

Cocking and Davey, "Gene Transfer in Cereals," *Science 236*: 1259–1262, 1987.

Düring, "Wound–Inducible Expression and Secretion of T4 Lysomzyme and Monoclonal Antibodies in Nicotiana Tabacum." Dissertation, University of Koln, FRG. pp. 13–16, 65–78, 87–89, 103–105, 108–110, 112–118, 120–126, and 135–158, (Jul. 9) 1988.

Düring and Hippe, "Synthesis, Assembly and Targeting of Foreign Chimeric Proteins in Transgenic Nicotiana Tabacum Cells," Biol. Chem. Hoppe Seyler, 370(9): 888, 1989.

Düring et al., "Synthesis and Self–Assembly of a Functional Monoclonal Antibody in Transgenic *Nicotiana tabacum*," *Plant Molecular Biology, 15*:281–293, 1990.

Edelman et al., "The Covalent Structure of an Entire γG Immunoglobulin Molecule", *Proc. Nat. Acad. Sci. USA 63*(1):78–85, 1969.

Eichholtz et al., "Expression of Mouse Dihydrofolate Reductase Gene Confers Methotrexate Resistance in Transgenic Petunia Plants" *Somatic Cell and Mol. Genet. 13*(1): 67–76 1987.

Emancipator and Lamm, "IgA Nephropathy: Overproduction of Decreased Clearance or Immune Complexes?" *Laboratory Investigation 61*(4): 365–367, 1989.

Ferkol et al., "Gene Transfer into Respiratory Epithelial Cells by Targeting the Polymeric Immunoglobulin Receptor," *J. Clin. Invest. 92*: 2394–2400, 1993.

(List continued on next page.)

Primary Examiner—T. D. Wessendorf
(74) Attorney, Agent, or Firm—Foley & Lardner

(57) ABSTRACT

Arrays of immunoglobulin binding proteins in plants or plant cells are provided. Such arrays comprise plants or plant cells transformed with polynucleotides encoding multiple different immunoglobulin binding proteins, or polypeptide components thereof. Methods are further provided for genetic segregation of the transformation events such that each transformant in an array is capable of producing progeny capable of expressing one or more immunoglobulin binding proteins, including multi-subunit proteins.

18 Claims, 2 Drawing Sheets

OTHER PUBLICATIONS

Frutiger et al., "Disulfide Bond Assignment in Human J Chain and Its Covalent Pairing with Immunoglobulin M," *Biochemistry 31*: 12643–12647, 1992.

Graves and Goldman, "The Transformation of *Zea mays* seedlings with Agrobacterium Tumefaciens," *Plant Molecular Biology 7*: 43–50, 1986.

Hammond, Elizabeth, "Ultrastructural Characteristics of Surface IgM Reactive Malignant Lymphoid Cells," *Experimental Cell Research 59*:359–370, 1970.

Heijne, "Signal Sequences the Limits of Variation," *J. Mol. Biol. 184*: 99–105, 1985.

Hein et al., "Evaluation of Immunoglobulins from Plant Cells," *Biotechnol. Prog. 7*: 455–461, 1991.

Hendrickson et al., "Altered Hepatic Transport of Immunoglobulin A in Mice Lacking the J Chain," *J. Exp. Med. 182*: 1905–1911, 1995.

Henneberg et al., "Antibrain Antibodies in Alcoholic Patients," *Alcohol & Alcoholism 28*(2) 181–187, 1993.

Hiatt et al. "Production of Antibodies in Transgenic Plants," *Nature 343*:76–78, 1989.

Horsch, et al., "A Simple and General Method for Transferring Genes into Plants," *Science 227*: 1229–1231, 1985.

Hunt, et al., "Plant Cells Do Not Properly Recognize Animal Gene Polyadenylation Signals," *Plant Molec. Biol. 8*: 23–25, 1987.

Janknecht and Nordheim, "Affinity Purification of Histidine–Tagged Proteins Transiently Produced in HeLa Cells," *Gene 121*: 321–324, 1992.

Kaetzel et al., "Epithelial Transcytosis of Monomeric IgA and IgG Cross–linked Through Antigen to Polymeric IgA. A Role for Monomeric Antibodies in the Mucosal Immune System," *Journal of Immunology 152*: 72–76, 1994.

Kaetzel et al., "The Polymeric Immunoglobulin Receptor (Secretory Component) Mediates Transport of Immune Complexes Across Epithelial Cells: A Local Defense Function for IgA," *Proc. Natl. Acad. Sci. 88*:8796–8800, 1991.

Kimball, John W., Introduction to Immunology, Macmillan, New York, "The Three Dimensional Structure of Immunoglobulins," pp. 264–265.

Kulseth and Rogne, "Cloning and Characterization of the Bovine Immunoglobulin J Chain cDNA and Its Promoter Region," *DNA and Cell Biology 13*(1):37–42, 1994.

LeFebvre et al. "Mammalian Metallothionein Functions in Plants," *Bio/Technology 5*(10): 1053–1056, 1987.

Lemaitre–Coelho et al., "In Vivo Experiments Involving Secretory Component in the Rat Hepatic Transfer of Polymeric IgA from Blood into Bile," *Immunology 43*:261–270, 1981.

Lütcke et al., "Selection of AUG Initiation Codons Differs in Plants and Animals," *EMBO J 6*: 43–48, 1987.

Ma et al., "Assembly of monoclonal antibodies with IgGL and IgA heavy chain domains in transgenic tobacco plants," *Eur. J. Immunol. 24*:131–138, 1994.

Mach, Jean–Pierre, "In vitro combination of human and bovine free secretory component with IgA of various species", *Nature 228*:1278–1282, 1970.

Mannik and Arend, "Fate of Preformed Immune Complexes in Rabbits and Rhesus Monkeys," *Journal of Experimental Medicine 134*: 19s–31s, 1971.

Max and Korsmeyer, "Human J Chain Gene. Structure and Expression in B Lymphoid Cells," *Journal of Experimental Medicine 161*: 832–849, 1985.

Mazanec et al., "Intracellular Neutralization of Influenza Virus by Immunoglobulin A Anti–Hemagglutinin Monoclonal Antibodies," *Journal of Virology 69*(2): 1339–1343, 1995.

Mestecky et al., "The Role of the Liver in Catabolism of Mouse and Human IgA," *Immunological Investigations 18*(1–4): 313–324, 1989.

Morton et al., "Purification and Characterization of Chimeric Human IgA1 and IgA2 Expressed in COS and Chinese Hamster Ovary Cells," *Journal of Immunology 151*(9): 4743–4752, 1993.

Nagura et al., "Translocation of Dimeric IgA Through Neoplastic Colon Cells In Vitro," *J. of Immunology 123*(5): 2359–2368, 1979.

Natvig et al., "Mechanism for Enhanced External Transfer of Dimeric IgA over Pentameric IgM," *J. of Immunology 159*:4330–4340, 1997.

Paul, William E. (ed.), *Fundamental Immunology*, Raven Press, New York, 1985, pp. 132–133.

Rifai et al., "Clearance Kinetics and Fate of Macromolecular IgA in Patients with IgA Nephropathy," *Laboratory Investigation 61*(4): 381–388, 1989.

Rifai and Mannik, "Clearance Kinetics and Fate of Mouse IgA Immune Complexes Prepared with Monomeric or Dimeric IgA," *J. of Immunology 130*(4): 1826–1832, 1983.

Sheldrake et al., "Selective Transport of Serum–Derived IgA into Mucosal Secretions," *J. of Immunology 132*(1): 363–368, 1984.

Tamer et al., "Comparative Studies Of Transcytosis and Assembly of Secretory IgA in Madin–Darby Canine Kidney Cells Expressing Human Polymeric Ig Receptor," *J. of Immunology 133*: 708–714, 1995.

Terskikh et al., "Dimeric Recombinant IgA Directed Against Carcino–Embryonic Antigen, a Novel Tool For Carcinoma Localization," *Molecular Immunology 31*(17): 1313–1319, 1994.

Thiele et al., "Mammalian Metallothionein Is Functional in Yeast," *Science 231*: 854–856, 1986.

Thorens and Vassalli, "Chloroquine and Ammonium Chloride Prevent Terminal Glycosylation of Immunoglobulins in Plasma Cells Without Affecting Secretion," *Nature 321*: 618–630, 1986.

Vaerman et al., "Lack of SC/pIgR–mediated epithellal Transport of a Human Polymeric IgA Devoid of J Chain: in Vitro and in Vivo Studies," *Immunology 95*: 90–96, 1998.

Valnes and Brandtzaeg, "Comparison of Paired Immunoflourescence and Paired Immunoenzyme Straining Methods Based on Primary Antisera form the Same Species," *J. of Histochemistry and Cytochemistry 30*(6): 517–523, 1982.

Vandekerckhove et al., "Enkephalins Produced in Transgenic Plants using Modified 2S Seed Storage Proteins," *Bio/technology 7*(9): 920–932, 1989.

Ward et al., "Binding Activities of a Repertoire of Single Immunoglobulin Variable Domains Secreted from *Escherichia coli*," *Nature 341*: 544–546, 1989.

Weissleder et al., "Quantitation of Slow Drug Release from an Implantable and Degradable Gentamicin Conjugate by In Vivo Magnetic Resonance Imaging," *Antimicrobial Agents and Chemotherapy 39*(4): 839–845, 1995.

Youngman et al., "Inhabition of IFN–γ Activity in Supernatants from Stimulated Human Intestinal Mononuclear Cells Prevents Up–Regulation of the Polymeric Ig Receptor in an Intestinal Epithelial Cell Line," *J. of Immunology 153*: 675–681, 1994.

Abstract of JP 58134032, esp@cenet database, Aug. 10, 1983.

Table 2
Representative Framework Region Sequences

1. Human Light Chains

| Type | FR1 | FR2 | FR3 | FR4 |
|---|---|---|---|---|
| Kappa I | DIQMTQSPSSLSASVGDRVTITC SEQ. ID NO: 74 | WYQQKPGKAPKLLIY SEQ. ID NO: 75 | GVPSRFSGSGSGTDFTLTISSLQPEDFATYYC SEQ. ID NO: 76 | FGQGTKVEIK SEQ. ID NO: 77 |
| Kappa II | DIVMTQSPLSLPVTPGEPASISC SEQ. ID NO: 78 | WYLQKPGQSPQLLIY SEQ. ID NO: 79 | GVPDRFSGSGSGTDFTLKISRVEAEDVGVYYC SEQ. ID NO: 80 | FGQGTKVEIK SEQ. ID NO: 77 |
| Kappa III | EIVLTQSPGTLSLSPGERATLSC SEQ. ID NO: 81 | WYQQKPGQAPRLLIY SEQ. ID NO: 82 | GIPDRFSGSGSGTDFTLTISRLEPEDFAVYYC SEQ. ID NO: 83 | FGQGTKVEIK SEQ. ID NO: 77 |
| Kappa IV | DIVMTQSPDSLAVSLGERATINC SEQ. ID NO: 84 | WYQQKPGQPPKLLIY SEQ. ID NO: 85 | GVPDRFSGSGSGTDFTLTISSLQAEDVAVYYC SEQ. ID NO: 86 | FGQGTKVEIK SEQ. ID NO: 77 |
| Lambda I | QSVLTQPPSVSOAPGQRVTISC SEQ. ID NO: 87 | WYQQLPGTAPKLLIY SEQ. ID NO: 88 | GVPDRFSGSKSGTSASLAINGLQSEDEADYYC SEQ. ID NO: 89 | FGGGTKLTVLG SEQ. ID NO: 90 |
| Lambda II | QSALTQPASVSGSPGQSITISC SEQ. ID NO: 91 | WYQQHPGKAPKLLIY SEQ. ID NO: 92 | GVPDRFSGSKSGNTASLTISGLQAEDEADYYC SEQ. ID NO: 93 | FGGGTKLTVLG SEQ. ID NO: 94 |
| Lambda III | SYELTQPPSVSVSPGQTARITC SEQ. ID NO: 95 | WYQQKPGQAPVLVIY SEQ. ID NO: 96 | GIPERFSGSNSGNTATLTISGVQAGDEAD{YC SEQ. ID NO: 97 | FGGGTKLTVLG SEQ. ID NO: 90 |
| Lambda IV | SELTQPPSVSVALOQTVRJTC SEQ. ID NO: 98 | WYQQKPGQAPLLVIY SEQ. ID NO: 99 | GIPDRFSGSSSGHTASLTITGAQAEDEADYYC SEQ. ID NO: 100 | FGGGTKLTVLG SEQ. ID NO: 90 |
| Lambda V | SALTQPPSASGSLGQSVTISC SEQ. ID NO: 101 | WYQQHPGRAPKLVIF SEQ. ID NO: 102 | GVPDRFSGSKSDQTASLTVSGLRAEDEADYYC SEQ. ID NO: 103 | FGGGTKLTVLR SEQ. ID NO: 104 |
| Lambda VI | NFMLTQPHSVSESPGKTVTISC SEQ. ID NO: 105 | WYQQRPGSAPITVW SEQ. ID NO: 106 | OVPDRFSGSSSNSASLTISGLKTEDEADYYC SEQ. ID NO: 107 | FGGGTKLTVLG SEQ. ID NO: 90 |

2. Mouse Light Chains

| Type | FR1 | FR2 | FR3 | FR4 |
|---|---|---|---|---|
| Kappa I | DIVMTQSPSSLAVSAGEKVTMSC SEQ. ID NO: 108 | WYQQKPGQSPKLLIY SEQ. ID NO: 109 | GVPSRFSGSGSGTDFTLTISSLQPEDFATYYC SEQ. ID NO: 110 | FGAGTKLEIK SEQ. ID NO: 111 |
| Kappa II | DIVMTQSPLSLPVTPGEPASISC SEQ. IDNO: 112 | WYLQKPGQSPKLLIY SEQ. IDNO: 113 | GVPDRFSGSGSGTDFTLKISRVEAEDVGVYYC SEQ. IDNO: 115 | FGGGTKLEIK SEQ. ID NO: 115 |
| Kappa III | EIVLTQSPGTLSLSPGERATLSC SEQ. IDNO: 116 | WYQQKPGQPPKLLIY SEQ. IDNO: 117 | GIPDRFSGSGSGTDFTLTISRLEPEDFAVYYC SEQ. IDNO: 118 | FGGGTKLEIK SEQ. ID NO: 115 |
| Kappa IV | DIVMTQSPDSLAVSLGERATINC SEQ. IDNO: 119 | WYQQKPGNSPKLWIY SEQ. IDNO: 120 | GVPDRFSGSGSGTDFTLTISSLQAEDVAVYYC SEQ. ID NO: 121 | FGAGTKLEIK SEQ. ID NO: 122 |
| Kappa V | DIQMTQSPSSLSASLGDRVTITC SEQ.IDNO: 123 | WYQQKPGGSPKLLIY SEQ. IDNO: 124 | GVPSRFSGSGSGTDYSLTISQLEQEDIATYFC SEQ. IDNO: 125 | FGGGTKLEIK SEQ. IDNO: 115 |
| Kappa VI | QIVLTQSPAIMSASPGEKVTMTC SEQ. ID NO: 126 | WYQQKSGTSPKRWIY SEQ. ID NO: 127 | GVPARFSGSLIGDLAALTITGAQTENEAIYFS SEQ. ID NO: 128 | FGAGTKLELK SEQ. ID NO: 111 |
| Lambda | QAVVTQESALTFSPGETVTLTC SEQ. IDNO: 129 | WVQEKPDHLFTGLIG SEQ. IDNO: 130 | GVPDRFSGSSSNSASLTISGLKTEDEADYYC SEQ. IDNO: 131 | FGGGTKLTVLG SEQ. IDNO: 132 |

FIG. 1A

3. Human Heavy Chains

| Group I | QVQLVQSGAEVKKPGASVKVSCKASGYTFT SEQ. ID NO: 133 | WVRGAPGQGLEWMG SEQ. ID NO: 134 | RVTITADTSTSTAYMELSSLRSEDTAVYYCAR SEQ. ID NO: 135 | WGQGITVTVSS SEQ. ID NO: 136 |
|---|---|---|---|---|
| Group II | QVQLQESGPGLVKPSQTLSLTCTVSGGSVS SEQ. ID NO: 137 | WTRQPPGKGLEWIIG SEQ. ID NO: 138 | RVTISVDTSKNQFSLKLSSVTAADTAVYYCAR SEQ. ID NO: 139 | WGQGFTVTVSS SEQ. ID NO: 136 |
| Group III | EVQLVESGGGLVQPGGSLRLSCAACGFTFS SEQ. ID NO: 140 | WVRQAPGKGLEWVS SEQ. ID NO: 141 | RFTISRDNSKNTLYLQMNSLRAEDTAVYYCAR SEQ. ID NO: 142 | WGQGUVTVSS SEQ. ID NO: 136 |

4. Mouse Heavy Chains

| Group IA | EVQLQESGPSLVKPSQTLSLTCSVTGDSIT SEQ. ID NO: 143 | WIRQFPGNKLEWMG SEQ. ID NO: 144 | RISITRDTSKNQYFLQLNSVREDTATYYCAR SEQ. ID NO: 145 | WGQGITVTVSS SEQ. ID NO: 146 |
|---|---|---|---|---|
| Group IB | QVQLKESGPGLVAPSQSLSITCTVSGFSLT SEQ. ID NO: 147 | WVRQPPGNKLEWMG SEQ. ID NO: 148 | RISISKDQSKSQVFLKMNSLQTDDTAMYYCAR SEQ. ID NO: 149 | WGQGTSVTVSS SEQ. ID NO: 150 |
| Group IIA | EVQLQQSGPELVKPGASVKISCKASGYTFT SEQ. ID NO: 151 | WVKQSPGKSLEWIG SEQ. ID NO: 152 | KATLTVDKSSSTAYMQLSSLTSEDSAVYYCAR SEQ. ID NO: 153 | WGQGUVTVSS SEQ. ID NO: 146 |
| Group IIB | QVQLQQPGAELVKPGASVKLSCKASGYTPT SEQ. ID NO: 154 | WVKQRPGQGLEWIG SEQ. ID NO: 155 | KATLTVDKSSSTAYMQLSSLTSEDSAVYYCAR SEQ. ID NO: 156 | WVQGTTVTVSS SEQ. ID NO: 157 |
| Group IIC | EVQLQQSGAELVKPGASVKLSCTASGFNIK SEQ. ID NO: 158 | WVRQPPGKALEWIA SEQ. ID NO: 159 | KATITADTSSNTAYLQLSLSSLTSEDTAVYYCAR SEQ. ID NO: 160 | WGQGTLVTVSS SEQ. ID NO: 161 |
| Group IIIA | EVKLVESGGGLVQPGGSLRLSCATSGFTES SEQ. ID NO: 162 | WVKQSPGKSLEWIG SEQ. ID NO: 163 | RFTVSRDTSQSHYLQMNNALRAEDTAIYYCAR SEQ. ID NO: 164 | WGAGTTVTVSS SEQ. ID NO: 165 |
| Group IIIB | EVKLLESGGGLVQPGGSLKLSCAASGFDES SEQ. ID NO: 166 | WVRQAPGKGLEWIG SEQ. ID NO: 167 | KFIISRDQAKQTLYLQMSKVRSEBTALYYCAR SEQ. ID NO: 168 | WGQGIITVTVSS SEQ. ID NO: 169 |
| Group IIIC | EVKLEESGGGLVQPGGSMKLSCVASGFTFS SEQ. ID NO: 170 | WVRQSPEKGLEWVA SEQ. ID NO: 171 | RFTISRDDSKSSVYLQMNNLRAEDTGIYYCU SEQ. ID NO: 172 | WGQGTLVTVSS SEQ. ID NO: 161 |
| Group IIID | EVQLVESGGGLVKPGGSLKLSCAASGFTFS SEQ. ID NO: 173 | WVRQTPEKRLEWVA SEQ. ID NO: 174 | RFTISRDQAKQTLYLQMSSLRSEDTAMYYCAR SEQ. ID NO: 175 | WGQGTSVTVSS SEQ. ID NO: 150 |
| Group VA | EVQLQQSGAELVRAGGSVKMSCKASGYTFT SEQ. ID NO: 176 | WVKQRPGQGLEWIG SEQ. ID NO: 177 | KYYLTVDKSSSTAYMQLRSLTSEDSAVYFCAR SEQ. ID NO: 178 | WGQGTLLTVSS SEQ. ID NO: 179 |
| Misc. | SEVQLVESGGGLVKPGGSVKLSCKASGFTFS SEQ. ID NO: 180 | WVRQAPGKGLEWVG SEQ. ID NO: 181 | RFTISRDNSKSTLYLQMSSLRSEDTATYYCAR SEQ. ID NO: 182 | WGQGTFVTVSS SEQ. ID NO: 146 |

FIG. 1B

IMMUNOGLOBULIN BINDING PROTEIN ARRAYS IN EUKARYOTIC CELLS

TECHNICAL FIELD

The present invention relates generally to arrays of immunoglobulin binding proteins. The invention is more particularly related to methods for the expression of arrays of foreign immunoglobulin binding proteins in eukaryotic cells, such as plant cells, as well as to transformed eukaryotic cells that express such arrays.

BACKGROUND OF THE INVENTION

Immunoglobulin molecules play key roles in a variety of physiological processes. Such molecules, which include antibodies and portions thereof, are critical for immune system function, and have found numerous therapeutic and diagnostic applications. The discovery of immunoglobulin molecules with desired binding characteristics is the focus of many current drug discovery efforts.

Traditional techniques for immunoglobulin molecule discovery involve the expression of a multitude of immunoglobulin molecule genes in an array of hybridoma cells, other forms of immortalized B-lymphocytes or phage-infected bacteria. For monoclonal antibody expression, individual antibody-producing B-lymphocytes from an immunized animal are generally fused with cells derived from an immortalized B-lymphocyte tumor. Clones of hybrid cells are then screened to identify those that grow indefinitely and secrete the desired immunoglobulin molecule. The polynucleotides encoding the monoclonal antibodies can then be isolated and used to express all or part of the antibody in other organisms, such as bacteria, yeast and plants. The ability to express immunoglobulins on the surface of bacteriophage has enabled the generation of immunoglobulin libraries that could represent all possible combinations of heavy and light chains derived from any population of B-lymphocytes. These libraries have been used successfully to identify high affinity combining sites recognizing a wide variety of antigens. A significant drawback to this technique is the randomization of heavy and light chain combining sites requiring the generation of very large numbers of recombinant phage to identify specific heavy and light chain binding pairs. This combinatorial aspect of random libraries makes expression of these libraries in other organisms unfeasible. Newer technologies involve transgenic mice expressing antibodies from human chromosomal segments which can be used to generate hybridoma arrays expressing human antibodies.

Arrays formed in B-lymphocytes, phage infected bacteria or transgenic animals have been useful within certain immunoglobulin molecule screens, but difficulties have been encountered with producing large quantities of immunoglobulin molecules in these cells. Large-scale production of immunoglobulin molecules from any of the traditional organisms is typically very expensive. Further, phage infected bacteria are incapable of providing the variety of immunoglobulin molecule structures that may be desired. Similarly, the usefulness of transgenic animal cells has been limited by the susceptibility of such cells to infection with viruses or other microorganisms.

For economic and other reasons, it would be desirable to use genetically engineered plants as the primary vehicle for the discovery of immunoglobulin molecules, as well as for the ultimate production of immunoglobulin molecules to be used in industrial, clinical or research applications. The advantages of plants for production of immunoglobulin molecules include a low cost of production, relatively low capital investment compared to fermentation systems, the absence of animal viruses and prions, production of the immunoglobulin molecule in a biochemical background of defined proteins such as seed proteins, ease of storage and transport, and a facile scale-up to unlimited quantities of raw material. It would also be desirable to be able to express a library of binding proteins that is not derived from a combinatorial process of randomly paired heavy and light chains.

It is known that immunoglobulin molecules can be expressed in a variety of eukaryotic hosts including plant cells. A wide variety of structural genes have been isolated from mammalian cells and viruses, joined to transcriptional and translational initiation and termination regulatory signals from a source other than the structural gene, and introduced into plant hosts in which these regulatory signals are functional. Among those host cells that have been transformed with individual immunoglobulin molecule-encoding nucleic acids are monocots (e.g., corn, rice and wheat), dicots (e.g., tobacco, soybean, alfalfa, petunia, and Arabidopsis) and lower plants (e.g., Chlamydomonas). Plants transformed with nucleic acids encoding individual immunoglobulin molecules have been able to produce fully functional and fully assembled immunoglobulins (see Hiatt et al., *Nature* 342:76–78, 1989; Firek et al., *Plant Molecular Biology* 23:861–870, 1993; Van Engelen et al., *Plant Molecular Biology* 26:1701–1710, 1994; Ma et al., *Science* 268:716–719, 1995; Magnuson et al., *Protein Expression and Purification* 7:220–228, 1996; Schouten et al., *Plant Molecular Biology* 30:781–793, 1996; Fiedler et al., *Immunotechnology* 3:205–216, 1997; Verch et al., *J. Immunol. Meth.* 220:69–75, 1998; Zeitlin et al., *Nature Biotechnology* 16:1361–1364, 1998; DeJaeger et al., *Eur. J. Biochem.* 259:426–434, 1999; Fischer et al., *Biol. Chem.* 380:825–839, 1999; Khoudi et al., *Biotechnology and Bioengineering* 64(2):135–143, 1999; McCormick et al., *Proc. Natl. Acad. Sci. USA* 96:703–708, 1999; Russell, *Curr. Top. Microbiol. Immunol.* 240:119–138, 1999).

In previous plant cell transformations, the transforming nucleic acid introduced a single immunoglobulin molecule. For example, tobacco plants have been transformed with individual gamma or kappa chains to produce individual plants expressing immunoglobulin molecule components. The respective tobacco transformants were then cross-pollinated to produce plants expressing a single antibody, wherein covalent bond formation between the two components resulted in the formation of enhanced binding capacity. In another instance, an antibody molecule was introduced into a single plant using a single vector. The vector encoded two immunoglobulin component chains and resulted in the formation, in the plant, of an immunoglobulin molecule comprising covalently linked heavy and light immunoglobulin chains.

Plant cells have not been used to express a diversity of immunoglobulin molecules in an array. As noted above, the ability to prepare an array of immunoglobulin molecules in plants or plant cells would facilitate identification of useful immunoglobulin molecules and would enable a rapid transition from immunoglobulin molecule discovery to full scale production in a single organism.

Accordingly, there remains a need in the art for methods for generating arrays of immunoglobulin molecules in plants and plant cells, as well as other eukaryotic organisms and cells. The present invention fulfills these needs and further provides other related advantages.

SUMMARY OF THE INVENTION

Briefly stated, the present invention provides methods for the production of arrays of biologically or physiologically active immunoglobulin binding proteins in eukaryotic cells. Within certain aspects, methods are provided for preparing an immunoglobulin binding protein array in plant cells, comprising the steps of: (a) transforming a population of plant cells with a library of at least two different polynucleotides encoding different immunoglobulin binding protein (IgBP) polypeptides that: (i) specifically bind to a ligand with a $K_D<10^{-6}$ moles/liter; or (ii) form one or more disulfide bonds with one or more polypeptides in the transfected cell, to generate a binding protein that specifically binds to a ligand with a $K_D<10^{-6}$ moles/liter; wherein the IgBP polypeptides (i) comprise four framework regions (e.g., human or murine) alternating with three complementarity determining regions and (ii) comprise at least one peptide sequence having at least 75%, preferably at least 95%, sequence identity to a framework region of a native IgM, IgG, IgA, IgD, IgE, IgY, kappa or lambda immunoglobulin molecule; and wherein the IgBP polypeptides are not detectably expressed by the plant cells prior to transformation; and (b) selecting transformed plant cells, and therefrom preparing an IgBP array in plant cells. Each IgBP polypeptide may be a functional IgBP or an IgBP component (e.g., a portion of an immunoglobulin molecule selected from the group consisting of heavy chains and fragments thereof, light chains and fragments thereof, J chains and secretory components) that, upon disulfide linkage to one or more IgBP components encoded by other polynucleotides in the library, forms a functional IgBP. Within certain specific embodiments, a library employed in such methods comprises at least 10, 100, 1,000 or 10,000 different polynucleotides.

Within certain embodiments, such methods further comprise the step of: (c) growing the transformed plant cells on a growth medium that supports replication of the plant cells, such that functional IgBPs are assembled by the plant cells. Within other specific embodiments, such methods further comprise the steps of: (c) growing the transformed plant cells on a growth medium to form plants; and (d) sexually crossing the plants with themselves or other plants to generate progeny, such that the progeny comprise polynucleotides encoding IgBP components sufficient to form a functional IgBP. Such progeny may be seeds, or may be plants or plant cells that assemble functional IgBPs, and the IgBP polypeptides may, but need not, be secreted from the plant cells.

The present invention further provides, within other aspects, methods for preparing a heavy chain binding protein array in eukaryotic cells (e.g., plant, insect or mammalian cells), comprising the steps of: (a) transforming a population of eukaryotic cells with a library of at least two different polynucleotides, wherein each polynucleotide encodes a different heavy chain binding protein ($C_HBP$) polypeptide that: (i) comprises an amino acid sequence that is at least 75% identical to a constant region tailpiece of a mu or alpha chain of a native immunoglobulin heavy chain; (ii) comprises multiple combining sites, wherein all of the combining sites satisfy the same one of the following requirements: (1) at least 75% identity to a 25 consecutive amino acid portion of an immunoglobulin light chain variable region or (2) at least 75% identity to a 25 consecutive amino acid portion of an immunoglobulin heavy chain variable region; and (iii) either (1) specifically binds to a ligand with a $K_D<10^{-6}$ moles/liter; or (2) forms one or more disulfide bonds with one or more polypeptides in the transfected cell, to generate a $C_HBP$ that specifically binds to a ligand with a $K_D<10^{-6}$ moles/liter; and (b) growing the transformed cells on a medium that permits assembly of $C_HBPS$, wherein each $C_HBP$ comprises at least four combining sites; and therefrom preparing a $C_HBP$ array in eukaryotic cells. The polynucleotides may, for example, encode immunoglobulin alpha or mu chains. Within certain embodiments, the cells are further transformed with one or more polynucleotides encoding polypeptides having sequences that are at least 75% identical to a sequence of an immunoglobulin J chain. Resulting $C_HBPs$ may be assembled, for example, from four alpha chains and one J chain, from twelve mu chains and/or from ten mu chain and at least one J chain. $C_HBPs$ or components thereof may, but need not, further comprise one or more portions of immunoglobulin molecules selected from the group consisting of J chains, secretory components and light chain constant regions. The $C_HBPs$ may accumulate in an intracellular compartment of the cells or may be secreted from the cells.

Within further aspects, methods are provided for preparing a heavy chain binding protein array in eukaryotic cells, comprising the steps of: (a) exposing multiple copies of a polynucleotide encoding a native heavy chain to a mutagen, such that random or site-directed mutagenesis of the polynucleotide occurs, resulting in a library of heavy chain variants; (b) transforming a population of eukaryotic cells with the library of heavy chain variants; and (c) growing the transformed cells on a medium that permits assembly of $C_HBPS$, wherein each $C_HBP$ comprises at least four combining sites; and therefrom preparing a $C_HBP$ array in eukaryotic cells.

Methods are further provided for preparing a plant $C_HBP$ array, comprising the steps of: (a) transforming a population of plant cells with a library of at least two different polynucleotides, wherein each polynucleotide encodes a different $C_HBP$ component that forms one or more disulfide bonds with one or more polypeptides in the transformed cell to generate a $C_HBP$ that specifically binds to a ligand with a $K_D<10^{-6}$ moles/liter, wherein each component: (i) comprises an amino acid sequence that is at least 75%, preferably at least 95%, identical to a constant region tailpiece of a mu or alpha chain of a native immunoglobulin heavy chain; and (ii) comprises multiple combining sites, wherein all of the combining sites satisfy the same one of the following requirements: (1) at least 75% identity to a 25 consecutive amino acid portion of an immunoglobulin light chain variable region or (2) at least 75% identity to a 25 consecutive amino acid portion of an immunoglobulin heavy chain variable region; (b) growing the transformed plant cells on a growth medium to form plants; and (c) sexually crossing the plants to generate progeny, such that the progeny comprise polynucleotides encoding $C_HBP$ components sufficient to form a functional $C_HBP$ that comprises at least four combining sites; and therefrom preparing a plant $C_HBP$ array. The progeny may be seeds, or may be plants or plant cells that assemble functional $C_HBPS$. Within certain specific embodiments, a library employed in such methods commprises at least 10, 100, 1,000 or 10,000 different polynucleotides. The $C_HBPs$ may accumulate in an intracellular compartment of the cells or may be secreted from the cells.

Within further aspects, the present invention provides $C_HBP$ arrays in eukaryotic cells, comprising at least two eukaryotic cells (e.g., plant, insect or mammalian cells) that are each transformed with a different polynucleotide encoding at least one $C_HBP$ polypeptide that: (a) comprises an amino acid sequence that is at least 75% identical to a constant region tailpiece of a mu or alpha chain of a native immunoglobulin heavy chain; (b) comprises multiple combining sites, wherein all of the combining sites satisfy the same one of the following requirements: (i) at least 75% identity to a 25 consecutive amino acid portion of an immunoglobulin light chain variable region or (i) at least 75% identity to a 25 consecutive amino acid portion of an immunoglobulin heavy chain variable region; (c) either (i) specifically binds to a ligand with a $K_D<10^{-6}$ moles/liter; or (ii) forms one or more covalent bonds with one or more polypeptides in the transfected cell, to generate a $C_HBP$ that specifically binds to a ligand with a $K_D<10^{-6}$ moles/liter; and (d) differs in amino acid sequence from other $C_HBPs$ in the array; wherein the cells assemble $C_HBPs$ comprising at least four combining sites. The polynucleotides may, for example, encode polypeptide components of immunoglobulin molecules independently selected from the group consisting of heavy chains and fragments thereof, light chains and fragments thereof, J chains and secretory components. Within certain specific embodiments, the cells in the array assemble at least 10, 100, 1,000 or 10,000 different polynucleotides. Also within certain embodiments, each cell in such an array may be transfected with at least two different polynucleotides, each encoding a different $C_HBP$ component, such that each cell assembles a functional $C_HBP$ comprising the $C_HBP$ components.

Within further aspects, the present invention provides compositions comprising an array of encapsulated $C_HBPS$, wherein each $C_HBP$: (a) comprises an amino acid sequence that is at least 75% identical to a constant region tailpiece of a mu or alpha chain of a native immunoglobulin heavy chain; (b) comprises at least four combining sites, wherein all of the combining sites satisfy the same one of the following requirements: (i) at least 75% identity to a 25 consecutive amino acid portion of an immunoglobulin light chain variable region; or (ii) at least 75% identity to a 25 consecutive amino acid portion of an immunoglobulin heavy chain variable region; and (c) either (i) specifically binds to a ligand with a $K_D<10^{-6}$ moles/liter; or (ii) forms one or more covalent bonds with one or more polypeptides in a cell, to generate a $C_HBP$ that specifically binds to a ligand with a $K_D<10^{-6}$ moles/liter; and (d) differs in amino acid sequence from other $C_HBPs$ in the array.

Methods are further provided for preparing a heavy chain binding protein array in eukaryotic cells, comprising the steps of: (a) exposing multiple copies of a polynucleotide encoding a native heavy chain to a mutagen, such that random or site-directed mutagenesis of the polynucleotide occurs, resulting in a library of heavy chain variants; (b) transforming a population of eukaryotic cells with the library of heavy chain variants; and (c) growing the transformed cells on a medium that permits assembly of $C_HBPS$, wherein each $C_HBP$ comprises at least four combining sites; and therefrom preparing a $C_HBP$ array in eukaryotic cells.

Within further aspects, the present invention provides $C_HBPs$ that: (a) comprise an amino acid sequence that is at least 75% identical to a constant region tailpiece of a mu or alpha chain of a native immunoglobulin heavy chain; (b) comprise at least four combining sites, wherein all of the combining sites satisfy the same one of the following requirements: (i) at least 75% identity to a 25 consecutive amino acid portion of an immunoglobulin light chain variable region; or (ii) at least 75% identity to a 25 consecutive amino acid portion of an immunoglobulin heavy chain variable region; and (c) either (i) specifically bind to a ligand with a $K_D<10^{-6}$ moles/liter; or (ii) form one or more covalent bonds with one or more polypeptides in a cell, to generate a $C_HBP$ that specifically binds to a ligand with a $K_D<10^{-6}$ moles/liter.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWING

FIGS. 1A–1B is a table depicting representative framework region (FR) sequences for human and mouse heavy and light chains, as indicated.

DETAILED DESCRIPTION OF THE INVENTION

As noted above, the present invention is directed to arrays of immunoglobulin binding protein (IgBP) polypeptides in eukaryotic organisms or cells, such as plants and plant cells. Each cell within such an array is transformed with at least one polynucleotide encoding one or more IgBPs or polypeptide components thereof (either integrated within the nuclear genome or resident in the cytoplasm). Within certain embodiments, each cell comprises polynucleotides encoding multiple polypeptide components of one or more IgBPs, such that each cell is capable of assembling at least one functional (i.e., biologically active) IgBP. Transformed cells may further comprise biologically active IgBPs, although in some cases (e.g., seeds generated from transformed plants), the functional IgBP may not be generated. Transgenic arrays embodying the present invention are useful for the discovery of novel IgBPs. Within certain embodiments, IgBPs within arrays provided herein are not derived from a combinatorial process of randomly paired heavy and light chains. It has been found, within the context of the present invention, that plants and other eukaryotic cells are capable of assembling IgBPs comprising any variable region (from light or heavy chain) expressed as specific heavy chain isotypes.

In certain embodiments, IgBP arrays may be generated in high yields in transformed, sexually reproducible plants. Transgenic plants provided herein are generally morphologically normal, but for the presence of one or more copies of the foreign polynucleotides in some or all of their cells. The respective gene products can be present in substantially all or a portion of the plant cells (e.g., the products can be localized to a cell type, tissue or organ). From the transgenic arrays, individual organisms or clones of cells can be identified rapidly, enabling the easy access to an economical, high yield process for the large scale production of a desired IgBP.

Glossary

Prior to setting forth the present invention in detail, definitions of certain terms used herein are provided.

Immunoglobulin binding protein (IgBP): An immunoglobulin binding protein (i) comprises an amino acid sequence that is at least 75% identical to at least one framework region of a native immunoglobulin molecule (e.g., IgM, IgG, IgA, IgD, IgE, IgY kappa or lambda) and (ii) is a functional binding protein. Framework regions are described below, under "Immunoglobulins." A protein P is a functional binding protein if (1) for one molecular, ionic or atomic ligand A the $K_D$ (P, A)$<10^{-6}$ moles/liter (preferably $<10^{-7}$ moles/liter), where $K_D(X,Y)=[X][Y]/[X:Y]$, and (2) for a different molecular, ionic or atomic species B, $K_D$ (P, B)$>10^{-4}$ moles/liter. Such a protein P is said to specifically bind A. Immunoglobulin binding proteins (IgBPs) generally function as a binding protein by virtue of the properties of a sequence of amino acids comprising a combining site, as defined below. An IgBP may comprise a single immunoglobulin chain or fragment thereof, multiple identical immunoglobulin chains or fragments thereof, or multiple non-identical immunoglobulin chains or fragments thereof. IgBPs include, for example, single chain antigen binding proteins, Fabs and Fvs. Also included are heavy chain binding proteins ($C_H$BPs), discussed in greater detail below.

Component of an IgBP: a polypeptide capable of forming one or more covalent bonds (preferably disulfide bonds) with one or more other polypeptides to generate a functional binding protein. A component is not itself a functional binding protein. For example, a multimeric antibody is considered an IgBP, and the polypeptide chains that are joined by covalent bonds to form an antigen binding site are considered to be IgBP components. Examples of such components include but are not limited to heavy chains and fragments thereof, light chains and fragments thereof, J chain and fragments thereof, and secretory component and fragments thereof.

IgBP polypeptide: encompasses both functional IgBPs and IgBP components.

Immunoglobulin heavy chain binding protein ($C_H$BP): an IgBP that (i) comprises multiple combining sites derived from (i.e., at least 75% identical to at least 25 consecutive amino acids of) either immunoglobulin light chain or heavy chain variable regions, but not both; and (ii) comprises a native heavy chain constant region sequence, or a fragment or other variant thereof, provided that the amino acid sequence of such a component is at least 75% identical to a constant region tailpiece (defined below) of a mu or alpha chain of a native immunoglobulin heavy chain. A $C_H$BP that comprises combining sites derived from one or more heavy chain variable regions does not comprise a combining site derived from a light chain variable region. Similarly, a $C_H$BP that comprises combining sites derived from one or more light chain variable regions does not comprise a combining site derived from a heavy chain variable region. Multiple $C_H$BP components may be covalently linked to generate a functional $C_H$BP, or a single polypeptide may be sufficient. Representative $C_H$BPs include proteins assembled from four alpha chains and one J chain, from twelve mu chains or from ten mu chains and at least on J chain.

Heavy chain binding protein ($C_H$BP) component: a polypeptide that is capable of forming one or more covalent bonds (preferably disulfide bonds) with one or more other polypeptides to generate a functional $C_H$BP. The component is not itself a binding protein. Examples of such components include, but are not limited to, heavy chains and fragments thereof, and J chain and fragments thereof.

Heavy chain binding protein ($C_H$BP) polypeptide: includes both $C_H$BPs and $C_H$BP components.

Immunoglobulin: any of the structurally related proteins or glycoproteins that function as antibodies. Polypeptides can be determined to comprise an immunoglobulin sequence based on sequence homology to known heavy chains, lights chains, J chains and related immunoglobulin sequences (see, e.g., Kabat et al., Sequences of Immunological Interest, National Institutes of Health, Bethesda, Md. 1991). In general, an immunoglobulin sequence should be at least 95% identical to a known immunoglobulin sequence over at least 50 consecutive amino acid residues of a constant region, if the immunoglobulin contains a constant region, and 75% identical to at least 25 consecutive amino acids of a variable region. Immunoglobulins may comprise multiple immunoglobulin components. Examples of such components include, but are not limited to, heavy chains and fragments thereof, light chains and fragments thereof, J chain and fragments thereof, and secretory component and fragments thereof. An immunoglobulin is generally identified by its binding specificity for a unique epitope.

Immunoglobulins are composed of the linear combination of a basic domain structure. Each domain contains two beta-pleated sheets, one beta sheet consisting of four beta strands, the other consisting of three beta strands. The two beta sheets are covalently linked by a disulfide bond. Antibody variable regions contain three sequences termed complementarity determining regions (CDR) within which are amino acid sequences of high variability when comparing numerous variable region sequences. Flanking each CDR are sequences of lesser variability termed framework regions (FR), of which there are four. The positions of the CDRs primarily coincide with the loops between beta strands, and conversely the FRs correlate with the beta strands themselves of the basic domain structure. For example, CDR1 (closest to the amino terminus of the immunoglobulin polypeptide) lies between beta strands 4-2 and 3-1, and CDR2 is between 3-1 and 4-4. The three stranded beta sheets of variable regions are the contact areas between the light chain and heavy chain variable regions. The following table illustrates the typical structure of variable regions.

TABLE 1

Amino Acid Residues Associated with Framework Regions and Complementarity Determining Regions of Immunoglobulin Light and Heavy Chain Variable Domains

| Segment | Light chain amino acids | Heavy chain amino acids |
| --- | --- | --- |
| FR1 | 1–23 | 1–30 |
| CDR1 | 24–34 | 31–35 |
| FR2 | 35–49 | 36–49 |
| CDR2 | 50–56 | 50–65 |
| FR3 | 57–88 | 66–94 |
| CDR3 | 89–97 | 95–102 |
| FR4 | 98–107 | 103–113 |

A polypeptide that is "at least 75% identical to a framework region of a native IgM, IgG, IgA, IgD, IgE, IgY, kappa or lambda immunoglobulin molecule" generally comprises a sequence that retains at least 75% amino acid sequence identity to a native FR region. The significance of similarity may be determined statistically using a computer program such as the Align program described by Dayhoff et al., *Meth. Enzymol.* 91:524–545, 1983. Representative FR sequences are presented in FIGS. 1A–1B, and others may be found, for example, in Kabat et al., Sequences of Immunological Interest, National Institutes of Health, Bethesda, Md. 1991.

Table 2 shows representative consensus sequences for mouse and human CDRs. The specific sequences of individual CDRs can be found in Kabat et al., Sequences of Immunological Interest, National Institutes of Health, Bethesda, Md. 1991. General rules for identifying a CDR are as follows: (1) CDR1 (light chain): start is approximately residue 24; residue before is always a Cys; residue after is always a Trp (typically TRP-TYR-GLN, but also, TRP-LEU-GLN, TRP-PHE-GLN, TRP-TYR-LEU); length 10 to 17 residues; (2) CDR 2 (light chain): start is always 16 residues after the end of CDR 1; residues before generally ILE-TYR, but also, VAL-TYR, ILE-LYS, ILE-PHE; length always 7 residues (except 7FAB which has a deletion in this region); (3) CDR 3 (light chain): start is always 33 residues after end of CDR 2 (except 7FAB which has the deletion at the end of CDR-L2); residue before is always Cys; residues after always PHE-GLY-XXX-GLY (SEQ ID NO: 1) (4) CDR 1 (heavy chain): start is approx residue 26 (always 4 after a CYS); residues before always CYS-XXX-XXX-XXX (SEQ ID NO: 2); residue after always a TRP; typically TRP-VAL, but also, TRP-ILE, TRP-ALA; (5) CDR 2 (heavy chain): start is always 15 residues after the end of CDR 1; residues before typically LEU-GLU-TRP-ILE-GLY (SEQ ID NO: 3), but there are a number of variations; residues after LYS/ARG-LEU/ILE/VAL/PHE/THR/ALA-THR/SER/ILE/ALA; (6) CDR 3 (heavy chain): start is always 33 residues after end of CDR 2 (always 2 after a CYS); residues before always CYS-XXX-XXX (typically CYS-ALA-ARG); residues after always TRP-GLY-XXX-GLY (SEQ ID NO: 4).

typical Align score of less than 3 indicates that the molecule being tested is a member of the immunoglobulin gene superfamily.

Combining site: a portion of a binding protein made up of those amino acid residues that contact the ligand or antigen by ionic interactions, hydrogen bonding, Van der Waals interaction or hydrophobic interaction. A combining site in a typical binding protein is located in a variable region of light and/or heavy chains and, more specifically, in a CDR of the light and/or heavy chains. A combining site need not comprise more than one polypeptide. A combining site generally comprises four FR and three CDR sequences, which alternate as displayed in Table 1. The precise amino acids present within a combining site may generally be

TABLE 2

CDR consensus sequences

| Type | CDR1 | CDR2 | CDR3 |
|---|---|---|---|
| *Light chain sequences.* | | | |
| Human kappa I | RASQSLVSISSYLA (SEQ ID NO: 5) | AASSLES (SEQ ID NO: 6) | QQYNSLPEWT (SEQ ID NO: 7) |
| Human kappa II | RSSQSLLHSDG DTYLN (SEQ ID NO:8) | LVSNRAS (SEQ ID NO: 9) | MQALQPRT (SEQ ID NO: 10) |
| Human kappa III | RASQSVSSSYLA (SEQ ID NO: 11) | GASSRAT (SEQ ID NO: 12) | QQYGSSPPLT (SEQ ID NO: 13) |
| Human kappa IV | KSSQSVLYSSNNKNYLA (SEQ ID NO: 14) | WASTRES (SEQ ID NO: 15) | QQYYSTPT (SEQ ID NO: 16) |
| Human lambda I | SGSSSNIIGNNYVS (SEQ ID NO: 17) | DNNKRPS (SEQ ID NO: 18) | ATWDDSLSANSAPV (SEQ ID NO: 19) |
| Human lambda II | TGTSSDVGGYNAVS (SEQ ID NO: 20) | DVTDRPS (SEQ ID NO: 21) | SSYGGGSNV (SEQ ID NO: 22) |
| Human lambda III | SGDNLGDKYVH (SEQ ID NO: 23) | DDNKRPS (SEQ ID NO: 24) | QAWDSSSDHPGVV (SEQ ID NO: 25) |
| Mouse kappa I | KSSQSLLNSGNQKNYLA (SEQ ID NO: 26) | WASTRES (SEQ ID NO: 27) | QNDYSYPLT (SEQ ID NO: 28) |
| Mouse kappa II | RSSQSLVHSNGNTYLE (SEQ ID NO: 29) | KVSNRFS (SEQ ID NO: 30) | FQGTHVPPYT (SEQ ID NO: 31) |
| Mouse kappa III | RASESVDSYGNSFMH (SEQ ID NO: 32) | AASNLES (SEQ ID NO: 33) | QQSNEDPPWT (SEQ ID NO: 34) |
| Mouse kappa IV | SASSSVSSSYLH (SEQ ID NO: 35) | RTSNLAS (SEQ ID NO: 36) | QQWSSYPGLT (SEQ ID NO: 37) |
| Mouse kappa V | RASQDDISNYLN (SEQ ID NO: 38) | YASRLHS (SEQ ID NO: 39) | QQGNTLPPRT (SEQ ID NO: 40) |
| Mouse kappa IV | SASSSVSYMH (SEQ ID NO: 41) | DTSKLAS (SEQ ID NO: 42) | QQWSSNPPMPLT (SEQ ID NO: 43) |
| *Heavy chain sequences.* | | | |
| Human heavy I | SYAIS (SEQ ID NO: 44) | WINPYGNGDTNYAQKFQG (SEQ ID NO: 45) | APGYGSGGGCYRGDYFDY (SEQ ID NO: 46) |
| Human heavy II | SYGWSWN (SEQ ID NO: 47) | RIYYRAYSGSTTYNPSLKS (SEQ ID NO: 48) | ELPGGYTGDDYYYGSGFDV (SEQ ID NO: 49) |
| Human heavy III | SYAMS (SEQ ID NO: 50) | VISGKTDGGSTYYADSVKG (SEQ ID NO: 51) | GRPGDSLSGYYYYYHYFDY (SEQ ID NO: 52) |
| Mouse heavy I | SGYWNNS (SEQ ID NO: 53) | YISGYSGSTYYNPSLKS (SEQ ID NO: 54) | GGYGYGYYYYDYYYYFDY (SEQ ID NO: 55) |
| Mouse heavy II | DYYMNN (SEQ ID NO: 56) | DINPGNGGTSYNQKFKG (SEQ ID NO: 57) | GSYYSSSYMAYYAFDY (SEQ ID NO: 58) |
| Mouse heavy III | DFYME (SEQ ID NO: 59) | ASRNKANDYTTEYSASVKG (SEQ ID NO: 60) | DYYYGSSYYEGPVYWYFDV (SEQ ID NO: 61) |

Immunoglobulin superfamily molecule: a molecule that has a domain size and amino acid residue sequence that is significantly similar to immunoglobulin or immunoglobulin related domains. The significance of similarity may be determined statistically as discussed above. A sequence identity of greater than 75% with the immunoglobulins listed in Kabat et al. (Sequences of Immunological Interest, National Institutes of Health, Bethesda, Md. 1991) indicates a member of the immunoglobulin superfamily. Also, a determined by x-ray diffraction analysis of the binding protein with bound ligand or antigen. See, for example, Amit et al., *Science* 233:4765, 747–53, 1986.

Immunoglobulin constant region: a portion of an immunoglobulin polypeptide that follows the carboxy terminus of the variable region. This is usually in the vicinity of amino acid #108 in light chains and amino acid #114 in heavy chains. Constant regions determine the isotype designation of the immunoglobulin and include but are not limited to kappa or lambda light chain constant regions and gamma, mu, alpha, epsilon and delta heavy chain constant regions. Constant regions of heavy chains are divided into domains. The first domain following the variable region is designated CH1. Domains following CH1 include the hinge region, CH2, CH3 and possibly CH4 and membrane spanning domain. Examples of immunoglobulin constant regions can be found in Kabat et al., Sequences of Immunological Interest, National Institutes of Health, Bethesda, Md. 1991.

Tailpiece of a constant region: tailpiece regions are located after the CH3 or CH4 segments of IgA or IgM constant regions, respectively. Examples of tailpieces are listed in Table 3. Other tailpiece regions may be identified based on similarity in sequences to one of the representative heavy chain tailpiece regions in Table 3. In general, a tailpiece should be at least 50% identical to a sequence in Table 3 and always contains a cysteine as the penultimate carboxy terminus amino acid. When co-expressed in appropriate eukaryotic cells containing an endomembrane system, tailpiece regions attached to either alpha or mu constant regions are capable of forming a disulfide bond between the penultimate cysteine of the tailpiece and a cysteine in J chain. Formation of these disulfide bonds can result in the polymerization of alpha or mu constant regions.

TABLE 3

Representative Heavy Chain Tailpiece Regions

| Isotype | Species | Sequence |
|---------|---------|----------|
| IgA | Human | PTHVNVSVVMAEVDGTCY (SEQ ID NO: 62) |
| IgA | Mouse | PTVNVIMSEGDGICY (SEQ ID NO: 63) |
| IgA | Mouse | PTNVSVSVIMSEGDGICY (SEQ ID NO: 64) |
| IgA | Rat | PTNVNVSVIMSEGDGICY (SEQ ID NO: 65) |
| IgA | Rabbit | PTHVNVSVVVADVEAVCY (SEQ ID NO: 66) |
| IgM | Human | PTLYNVSLVMSDTAGTCY (SEQ ID NO: 67) |
| IgM | Human | PTLYNVSLIMSDTGGTCY (SEQ ID NO: 68) |
| IgM | Hamster | PTLYNVSLIMSDAGGTCY (SEQ ID NO: 69) |
| IgM | Hamster | PTLYNVSLVLSDTAGZCY (SEQ ID NO: 70) |
| IgM | Rat | PTLYNVSLIMSDTASTCY (SEQ ID NO: 71) |
| IgM | Chicken | PSFVNVSLVLMDTVNSCN (SEQ ID NO: 72) |

J chain: a polypeptide that is substantially identical (i.e., at least 80% identical) in sequence to a J chain of Kabat et al. (Sequences of Immunological Interest, National Institutes of Health, Bethesda, Md. 1991). J chains are further capable of forming disulfide bonds to the penultimate cysteine residues in the tailpiece region of alpha or mu constant regions, thereby forming a polymeric structure, such as a dimeric IgA or a pentameric IgM. Disulfide bonds between J chain and alpha or mu heavy chain constant regions are generally formed in the endomembrane system of a cell during the process of secretion. The presence of disulfide bonds can be measured by comparison of the polypeptides in the presence or absence of an appropriate reducing agent such as dithiothreitol or mercaptoethanol. Comparative analysis of peptides can be accomplished by, for example, denaturing gel electrophoresis using SDS and polyacrylamide as described in Molecular Cloning: A Laboratory Manual, Sambrook et al., eds., Cold Spring Harbor Laboratory, Cold Spring Harbor, N.Y. (1989) and Antibodies: A Laboratory Manual, Harlow and Lane, eds., Cold Spring Harbor, N.Y. (1988).

Alpha chain: a polypeptide that is substantially identical (i.e., at least 90% identical) in sequence to the constant region of an alpha chain of Kabat et al. (Sequences of Immunological Interest, National Institutes of Health, Bethesda, Md. 1991).

Mu chain: a polypeptide that is substantially identical (i.e., at least 90% identical) in sequence to the constant region of a mu chain of Kabat et al. (Sequences of Immunological Interest, National Institutes of Health, Bethesda, Md. 1991).

Secretory component: a polypeptide that binds to polymeric immunoglobulins containing J chains. Secretory components are derived from the polyimmunoglobulin receptor. The sequences of some secretory components and polyimmunoglobulin receptors have been determined. Other polypeptide that share at least 75% sequence identity with a known secretory component, and that retain the ability to bind to polymeric immunoglobulins containing J chains, are also considered to be secretory components.

Heavy chain: a polypeptide that comprises an amino acid sequence that is at least 90% identical to the constant region of a native heavy chain sequence and an amino acid sequence that is at least 75% identical to the variable region of a native heavy chain sequence (see Kabat et al., Sequences of Immunological Interest, National Institutes of Health, Bethesda, Md. 1991) and that, when co-expressed with a light chain in the endomembrane system of an appropriate eukaryotic cell is capable of forming a heavy chain-light chain complex, potentially an antibody, joined by disulfide bonding. Heavy chains may be identified as the larger of the two polypeptides present within a divalent antibody, Fab, Fab'2 or Fv. Heavy chains are also found as components of polyvalent antibodies such as IgAs and IgMs.

Light chain: a polypeptide that is at least 90% identical to the constant region of a native light chain sequence and 75% identical to the variable region of a native light chain sequence (see Kabat et al., Sequences of Immunological Interest, National Institutes of Health, Bethesda, Md. 1991) and that when co-expressed with a heavy chain in the endomembrane system of an appropriate eukaryotic cell is capable of forming a heavy chain-light chain complex, potentially an antibody, joined by disulfide bonding. Light chains may be identified as the smaller of the two polypeptides present within a divalent antibody, Fab, Fab'2 or Fv. Light chains are also found as components of polyvalent antibodies such as IgAs and IgMs.

Light chain or heavy chain variable region: a region of a light chain or heavy chains that contains three complementarity determining regions (CDR), flanked by four framework regions (FR), as discussed above. A variable region generally has two antiparallel β-pleated sheets, one of which consists of four β strands, and one of which consists of three β strands. In an antibody the three-stranded sheet is the contact area between heavy chain and light chain variable regions. The two β-pleated sheets are covalently linked by a disulfide bond (the half cystines that form this bond are conserved). The CDRs coincide with the loops between β strands, while the FRs correlate with the β strands themselves. An IgBP that does not comprise a light chain variable region generally does not contain a polypeptide that contains CDRs or FRs but may contain the constant region of a light chain.

IgBP array: a population of eukaryotic cells or organisms (e.g., plants) that are transformed with different polynucleotides, each of which encodes a different IgBP or polypeptide component thereof. Each cell or organism is transformed with at least one such polynucleotide, and preferably at least two such polynucleotides, such that the array comprises at least two organisms or cells that are transformed with different polynucleotides. In general, the IgBP polypeptides encoded by the polynucleotides should not be detectably expressed by untransformed cells or organisms. An array may be displayed on a growth surface that allows for the replication of the cells or organisms. An array may be present, for example, in plants or plant cells, or may be stored in seed form.

Dicotyledon (dicot): A flowering plant whose embryos have two seed halves or cotyledons. Examples of dicots are: tobacco; tomato; the legumes including alfalfa; oaks; maples; roses; mints; squashes; daisies; walnuts; cacti; violets; and buttercups.

DNA: Deoxyribonucleic acid.

Epitope: A portion of a molecule that is specifically recognized by an immunoglobulin. It is also referred to as the determinant or antigenic determinant.

Eukaryotic hybrid vector: A DNA molecule by means of which DNA coding for a polypeptide (insert) can be introduced into a eukaryotic cell.

Fab fragment: A polypeptide consisting of a portion of an antibody molecule containing the active portions of an antibody heavy chain and an antibody light chain covalently coupled together and capable of specifically combining with antigen. Fab fragments are typically prepared by proteolytic digestion of substantially intact antibody molecules with papain using methods that are well known in the art. However an Fab fragment may also be prepared by expressing in a suitable host cell the desired portions of an antibody heavy chain and light chain using methods well known in the art.

Fv fragment: A polypeptide consisting of the active portions of an antibody heavy chain variable region and an antibody light chain variable region covalently coupled together and capable of specifically combining with antigen. Fv fragments are typically prepared by expressing in a suitable host cell the desired portions of antibody heavy chain variable region and light chain variable region using methods well known in the art.

Mutagenesis: A process whereby the nucleotide sequence of an original polynucleotide is changed in one or a few locations to produce derivative polynucleotides of substantially the same sequence. Mutagenesis can be accomplished by manipulation of polynucleotides in vitro by, for example, using various commonly available enzymes and mutagenic oligonucleotides. Mutagenesis can also be accomplished in vivo using the immune system of an animal to introduce desired changes in polynucleotides encoding immunoglobulins for example. B cell maturation, for example, is a process whereby a mutated polynucleotide is derived from an original polynucleotide.

Insert: A DNA sequence foreign to the host, consisting of a structural gene and optionally additional DNA sequences.

(Selective) Genetic marker: A DNA sequence coding for a phenotypical trait by means of which transformed cells can be selected from untransformed cells.

Leader sequence: A contiguous series of amino acids preceding a polypeptide. The leader sequence may be cleaved from the polypeptide during the process of secretion.

Signal Sequence: A DNA sequence coding for an amino acid sequence attached to the polypeptide which binds the polypeptide to the endoplasmic reticulum and is essential for protein secretion.

Lower plant: Any non-flowering plant including ferns, gymnosperms, conifers, horsetails, club mosses, liverworts, hornworts, mosses, red algae, brown algae, gametophytes, sporophytes of pteridophytes, and green algae (e.g., Chlamydomonas).

Monocotyledon (monocot): A flowering plant whose embryos have one cotyledon or seed leaf. Examples of monocots are: lilies; grasses; corn; rice; grains, including oats, wheat and barley; orchids; irises; onions and palms.

Open reading frame: A sequence of nucleic acids when read sequentially three at a time (triplets) contains no stop codon sequences. Stop codon sequences are UAG, UAA, and UGA.

Paratope: An antigen binding site of an antibody molecule.

Plant cell: A cell that depends for its growth on light and contains chloroplasts.

Pollination: the transfer of pollen from male to female flower parts. "Self-pollination" refers to the transfer of pollen from male flower parts to female flower parts on the same plant. This process typically produces seed from which progeny plants can be grown. "Cross-pollination" is the transfer of pollen from the male flower parts of one plant to the female flower parts of another plant. This process typically produces seed from which viable progeny can be grown.

Polypeptide and peptide: A series of amino acid residues covalently connected one to the other by peptide bonds between the alpha-amino and carboxy groups of adjacent residues or by disulfide bridges between two cysteines.

Protein: A linear series of greater than about 50 amino acid residues connected one to the other as in a polypeptide.

Promoter: A recognition site on a DNA sequence or group of DNA sequences that provide an expression control element for a gene and to which RNA polymerase specifically binds and initiates RNA synthesis (transcription) of that gene. An "inducible promoter" is a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like. A "viral promoter" is a promoter with a DNA sequence substantially similar to the promoter found at the 5' end of a viral gene. A typical viral promoter is found at the 5' end of the gene coding for the p21 protein of MMTV described by Huang et al., Cell 27:245, 1981. A "synthetic promoter" is a promoter that was chemically synthesized rather than biologically derived. Usually synthetic promoters incorporate sequence changes that optimize the efficiency of RNA polymerase initiation. A "constitutive promoter" is a promoter where the rate of RNA polymerase binding and initiation is approximately constant and relatively independent of external stimuli. Examples of constitutive promoters include the cauliflower mosaic virus 35S and 19S promoters described by Poszkowski et al., EMBO J. 3:2719, 1989 and Odell et al., Nature 313:810, 1985. A "temporally 25 regulated promoter" is a promoter where the rate of RNA polymerase binding and initiation is modulated at a specific time during development. Examples of temporally regulated promoters are given in Chua et al., *Science* 244:174–181, 1989. A "spatially regulated promoter" is a promoter where the rate of RNA polymerase binding and initiation is modulated in a specific structure of the organism such as the leaf, stem or root. Examples of spatially regulated promoters are given in Chua et al., *Science* 244:174–181, 1989. A "spatiotemporally regulated promoter" is a promoter where the rate of RNA polymerase binding and initiation is modulated in a specific structure of the organism at a specific time during development. A typical spatiotemporally regulated promoter is the EPSP synthase-35S promoter described by Chua et al., *Science* 244:174–181, 1989.

RNA: Ribonucleic acid.

rRNA: Ribosomal RNA.

Secretion signal: A contiguous series of amino acids attached to or contained within a polypeptide which enables secretion of the polypeptide from a cell. The amino acids may or may not be cleaved from the polypeptide during the process of secretion.

Seed: A viable dormant embryo enclosed in a testa that is derived from the integument(s). The embryo is associated with food reserve organs.

Single-chain antigen-binding (SCAB) protein: A polypeptide composed of an immunoglobulin light-chain variable region amino acid sequence ($V_L$) tethered to an immunoglobulin heavy-chain variable region amino acid sequence ($V_H$) by a peptide that links the carboxyl terminus of the $V_L$ sequence to the amino terminus of the $V_H$ sequence or by a peptide that links the amino terminus of the $V_L$ sequence to the carboxyl terminus of the $V_H$ sequence.

Single-chain antigen-binding (SCAB) protein-coding gene: A recombinant gene coding for a single-chain antigen-binding protein.

Structural gene: A gene coding for a polypeptide and being equipped with a suitable promoter, termination sequence and optionally other regulatory DNA sequences, and having a correct reading frame.

T-DNA: A segment of transferred DNA specific for plants.

Ti-plasmid: Tumor-inducing plasmid specific for plants.

Ti-DNA: A segment of DNA from Ti-plasmid.

Transfection: A process whereby foreign DNA is introduced into a eukaryotic cell. The process may or may not result in cellular transformation.

Transformation: A process whereby foreign DNA is introduced into the genome or cytoplasm of an organism resulting in the expression of a trait that did not previously exist in the organism. Examples of added traits are resistance to toxic chemicals and expression of foreign proteins not normally produced by the organism.

Immunoglobulin Binding Proteins (IgBP) Polypeptides

As noted above, IgBPs comprise one or more polypeptides in which amino acids are linked by covalent peptide bonds. In general, an IgBP (i) comprises an amino acid sequence that is at least 75% identical to at least one framework region of a native immunoglobulin molecule (e.g., IgM, IgG, IgA, IgD, IgE, IgY, kappa or lambda) and (ii) is a functional binding protein. Sequence identity may be determined using any of a variety of well known algorithms, which may be readily optimized by those of ordinary skill in the art. One such algorithm is employed by the Align program described by Dayhoff et al., *Meth. Enzymol.* 91:524–545, 1983. A functional binding protein, as discussed above, specifically binds to a ligand with a $K_D < 10^{-6}$ moles/liter (preferably $<10^{-7}$ moles/liter). $K_D$ may be readily determined using well known assays.

An IgBP may comprise a single immunoglobulin chain or fragment thereof, multiple identical immunoglobulin chains or fragments thereof, or multiple non-identical immunoglobulin chains or fragments thereof. IgBPs include, for example, single chain antigen binding proteins, Fabs and Fvs. Other IgBPs are heavy chain binding proteins ($C_H$BPs), which comprise multiple combining sites composed of amino acid residues derived from the constant region of an immunoglobulin heavy chain and a variable region from any source (e.g., either heavy or light chain, but not both). In a preferred embodiment the variable region is derived from a heavy chain. $C_H$BPs further comprise an amino acid sequence that is at least 75% identical to a constant region tailpiece of a mu or alpha chain of a native immunoglobulin heavy chain. A $C_H$BP may further comprise one or more J chains, which can serve to link other component polypeptides. Representative $C_H$BPs include proteins assembled from four alpha chains and one J chain, from twelve mu chains or from ten mu chains and at least on J chain.

IgBPs may be made up of component polypeptides linked by covalent bonds, preferably disulfide bonds. Preferred components comprise one or more portions of immunoglobulin molecules such as heavy chains and fragments thereof, light chains and fragments thereof, J chains and fragments thereof and secretory components and fragments thereof. A component polypeptide may comprise a native immunoglobulin sequence or a variant of such a sequence. As noted above, an "IgBP polypeptide" is any polypeptide that is a functional IgBP or an IgBP component.

For preparation of an array, a library of polynucleotides encoding IgBP polypeptides is generally employed. Such a library generally comprises at least two different polynucleotides (preferably at least 10, 100, 1,000 or 10,000 different polynucleotides), each of which encodes a different IgBP or component thereof. An IgBP is different from another IgBP if there are one or more differences between the amino acid sequences of the IgBPs. Preferably, such differences result in differences in the affinity of the IgBP for a respective substrate, ligand or epitope. Preferred libraries encode variants of an original polynucleotide. Such a library may be derived from the original polynucleotide by a process of mutagenesis that may occur in vitro (e.g., using commonly available enzymes and mutagenic oligonucleotides) or in vivo (e.g., by B cell maturation). Such a library generally comprises polynucleotides encoding variants that differ from an original immunoglobulin by one or more amino acid substitutions and/or deletions, such that each variant retains at least 75% identity, preferably at least 95% identity, to the original immunoglobulin. Certain such libraries may contain polynucleotides encoding immunoglobulin variants that differ from the original immunoglobulin only in one or more point mutations. Polynucleotides in a library are preferably present within a vector that facilitates transformation of target eukaryotic cells, and subsequent expression of binding protein or component thereof in transformed cells.

There are a variety of sources for nucleic acids encoding populations of immunoglobulin binding proteins. For example, immunoglobulins may be derived from the B cells of an immunized host. Such a population of immunoglobulin binding proteins is derived from a multitude of cells each expressing a different immunoglobulin binding protein. Populations of immunoglobulin binding proteins or potential immunoglobulin binding proteins can also be derived from the mutagenesis of unique sequences of immunoglobulins.

Methods for isolating polynucleotides encoding a population of IgBPs are well known in the art. See, for example, Molecular Cloning: A Laboratory Manual, Sambrook et al., eds., Cold Spring Harbor Laboratory, Cold Spring Harbor, N.Y. (1989) and Antibodies: A Laboratory Manual, Harlow and Lane, eds., Cold Spring Harbor, N.Y. (1988). As noted above, particularly preferred polynucleotides encode immunoglobulin heavy and light chain variable regions, or portions thereof. Such polynucleotides may be isolated from cells obtained from a vertebrate, preferably a mammal, which has been immunized with an antigenic ligand (antigen) against which activity is sought (i.e., a preselected antigen). The immunization can be carried out conventionally and antibody titer in the animal can be monitored to determine the stage of immunization that corresponds to the affinity or avidity desired. Partially immunized animals typically receive only one immunization and cells are collected therefrom shortly after a response is detected. Fully immunized animals display a peak titer that is achieved with one or more repeated injections of the antigen into the host mammal, normally at two to three week intervals. Usually three to five days after the last challenge, the spleen is removed and the genes coding for immunoglobulin heavy and immunoglobulin light chains are isolated from the rearranged B cells present in the spleen using standard procedures. See Current Protocols in Molecular Biology, Ausubel et al., eds., John Wiley and Sons, New York (1987) and Antibodies: A Laboratory Manual, Harlow and Lane, eds., Cold Spring Harbor, N.Y. (1988).

In addition to the spleen, rearranged B cells can be derived from the bone marrow of individuals who have been exposed to specific antigens. For example, patients in hospitals can be exposed to infectious organisms that they would not ordinarily encounter. Frequently, these patients mount an immune response that results in B cell maturation and deposition in bone marrow of B cells expressing antibodies that neutralize the pathogen. In addition to nosocomial exposure, memory B cells are deposited in response to a variety of infections, including HIV, HPV, HSV and CMV.

Genes encoding $V_H$ and $V_L$ polypeptides can be derived from cells producing IgA, IgD, IgE, IgG or IgM, and most preferably from IgG producing cells. Methods for preparing fragments of genomic DNA from which immunoglobulin variable region genes can be cloned are well known in the art. See for example, Herrmann et al., *Methods in Enzymol.* 152:180–183, 1987; Frischauf, *Methods in Enzymol.* 152:183–190, 1987; and Frischauf, *Methods in Enzymol.* 152:199–212, 1987.

Probes useful for isolating polynucleotides encoding immunoglobulin products include the sequences encoding constant portions of the $V_H$ and $V_L$, sequences encoding the framework regions of $V_H$ and $V_L$ and probes for the constant region of the entire rearranged immunoglobulin gene, these sequences being obtainable from available sources. See, for example, Early and Hood, Genetic Engineering, Setlow and Hollaender eds., Vol. 3:157–188, Plenum Publishing Corporation, New York (1981); and Kabat et al., Sequences of Immunological Interest, National Institutes of Health, Bethesda, Md. (1991). Polynucleotides encoding a polypeptide subunit or component of an IgBP can be isolated from either the genomic DNA containing the gene expressing the polypeptide or the messenger RNA (mRNA) that codes for the polypeptide. The use of mRNA is preferred, due to the difficulty in juxtaposing sequences of genomic DNA that encode the polypeptide, where the sequences are separated by introns. In such cases, the DNA fragment(s) containing the proper exons must be isolated, the introns excised, and the exons spliced together in the proper order and orientation. Methods for isolating mRNA coding for peptides or proteins are well known in the art. See, for example, Current Protocols in Molecular Biology, Ausubel et al., John Wiley and Sons, New York (1987); "Guide to Molecular Cloning Techniques", in Methods In Enzymology, Volume 152, Berger and Kimmel, eds. (1987); and Molecular Cloning: A Laboratory Manual, Sambrook et al., eds., Cold Spring Harbor Laboratory, Cold Spring Harbor, N.Y. (1989).

Mutagenesis can be used to generate a multitude of polynucleotides encoding different variants of native IgBPs, which can then be resolved by expression in an array of eukaryotic cells or plant cells or plants as provided herein. Mutant proteins may be obtained in which one or more specific changes in the codons of a gene of choice are introduced. One or a few polypeptides are then expressed for evaluation of binding properties. At the other extreme is random mutagenesis, by means of relatively nonspecific changes of codons at a variety of sites in the gene of choice. Arrays of plants and plant cells, as well as other eukaryotic cells, can be used for functional screens of mutant IgBPs. Preferably, polynucleotides within such arrays encode variants that differ from a native IgBP sequence in one or more amino acid substitutions and/or deletions, such that each variant retains at least 75%, preferably at least 95%, identity to the native IgBP. Particularly preferred are arrays in which each polynucleotide differs from the native IgBP in one or more point mutations. Mutagenesis is also a process that occurs naturally during the development of antibodies. During the course of B cell maturation, antibody-encoding genes are recombined, selected, and mutated to produce plasma cells that encode antibodies with higher affinity for an antigen compared to the original polynucleotide encoding the antibody with specificity for the same antigen.

Regardless of the precise type of IgBP, array polynucleotides are formulated so as to permit entry into, and replication within, a target host cell. For certain transfection techniques, the polynucleotides are cloned into a suitable expression vector. Any vector can be used for such transfection, provided that the vector is capable of the transcription of IgBP genes as well as selectable markers in a target cell. Typical expression vectors useful for expression of genes in plants are well known in the art and include vectors derived from the tumor-inducing (Ti) plasmid of *Agrobacterium tumefasciens* described by Rogers et al., *Meth. in Enzymol.* 153:253–277, 1987. However, several other expression vector systems are known to function in plants. See, for example, Register et al., *Plant Mol Biol.* 25:951–961, 1994; Verch et al., *J Immunol. Meth.* 220:69–75, 1998.

Alternatively, for certain transfection techniques an expression vector is unnecessary or undesirable. In these cases, either single or multiple DNA fragments containing the polypeptide coding genes linked to plant expression control elements (expression cassettes) are introduced directly into target plant cells. The DNA fragment used to transfect plant cells may include either single or multiple polypeptide coding genes.

Suitable expression vectors and cassettes generally contain expression control elements, which include the promoter. The polypeptide coding genes are operatively linked to the expression vector or cassette to allow the promoter sequence to direct RNA polymerase binding and synthesis of the desired polypeptide coding gene. Useful in expressing the polypeptide coding gene are promoters that are inducible, viral, synthetic, constitutive, temporally regulated, spatially regulated and/or spatiotemporally regulated. The choice of expression vector, and ultimately the selection of a promoter to which the polypeptide coding gene is operatively linked, depends directly (as is well known in the art) on the functional properties desired (e.g., the location and timing of protein expression and the host cell to be transformed). However, an expression vector or cassette useful in practicing the present invention is at least capable of directing the replication, and preferably also the expression, of the polypeptide coding gene included in the DNA segment to which it is operatively linked.

In preferred embodiments, the expression vector or cassette used to express the polypeptide-coding genes includes a selection marker that is effective in a target cell, preferably a drug resistance selection marker. Alternatively, a separate vector or expression cassette comprising a selection marker may be co-transfected. A preferred drug resistance marker is the gene whose expression results in kanamycin resistance (e.g., the chimeric gene containing the nopaline synthase promoter, Tn5 neomycin phosphotransferase II and nopaline synthase 3' nontranslated region described by Rogers et al., in Methods For Plant Molecular Biology, a Weissbach and H. Weissbach, eds., Academic Press Inc., San Diego, Calif. (1988)). Useful plant expression vectors include pMON 530, pKYLX and pUC. Another preferred drug resistance marker is the gene for phosphinothricin acetyltransferase, PAT, which confers resistance to Liberty herbicide. Alternatively, the selection marker could permit the growth of the transfected cells or tissue on a alternative substrate present in the medium (e.g., xylA gene; Haldrup et al., *Plant Mol Bio* 37(2):287–296, 1998).

A variety of methods have been developed to operatively link DNAs to vectors via complementary cohesive termini. For instance, complementary homopolymer tracks can be added to the DNA segment to be inserted and to the vector DNA. The vector and DNA segment are then joined by hydrogen bonding between the complementary homopolymeric tails to form recombinant DNA molecules. Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteria phage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass. Polymerase chain reaction (PCR) can also be used to introduce appropriate restriction sites into polynucleotide sequences as would be needed for ligating the polynucleotide into a restriction site in a plant or eukaryotic cell expression vector.

Immunoglobulin Binding Proteins (IgBP) Arrays

A library of polynucleotides as described above may be used to generate an array in eukaryotic cells or organisms (e.g., plants or seeds) using standard transfection techniques appropriate for the cell or organism of interest. In general, a library is used to transfect a population of eukaryotic cells such that some or all of the cells contain one or more polynucleotides encoding IgBP polypeptides that are not be detectably expressed by untransfected cells. Such transfection can result in functional transformation, which permits the cells to produce IgBPs and/or components thereof. The cells may then be grown on an appropriate medium to allow for replication and the functional expression of IgBPs or components thereof. Optionally, a progeny population may be created from a sexual cross of transformants expressing IgBP components, such that some or all of the progeny population contain polynucleotides encoding sufficient IgBP components to form functional IgBPs. Also optionally, progeny populations may be created from sexual crosses of transformants expressing multiple IgBPs such that each member of the progeny population expresses a single functional IgBP. Sexual crosses between plants expressing IgBPs, or between wild-type plants and plants expressing IgBPs, results in the genetic segregation of the various IgBPs among the various progeny seeds or progeny plants. As such, some of the progeny will express a single IgBP.

Transformed organisms are generally morphologically normal but for the presence of the foreign genes in some or all of their cells. The genes can be present in one copy or multiple copies in some or all of the cells. The respective gene products can be present in substantially all or a portion of the cells (i.e., the products can be localized to a cell type, tissue or organ). Transformed cells may be dormant (e.g., non-germinating seeds), present in culture or in an intact organism.

Transgenic cells or organisms (such as plants) may be produced, in one embodiment, by introducing into the nuclear genome a mammalian gene or genes that code for a multiplicity of IgBPs. In another embodiment, the introduced gene or genes remain extrachromasomal after being introduced by viral infection. In each single organism or population of cells, one or more copies of the nucleic acid encoding the IgBP polypeptide(s) is integrated into the genome or is resident in the cytoplasm. Since a multiplicity of open reading frames is used in the transformation, one or more nucleic acids encoding IgBP polypeptides with different specificities can be introduced into each cell or population of cells. Transformation techniques that result in multiple copies of nucleic acids integrated into the nucleus of a plant cell include Agrobacterium mediated transformation, biolistic transformation, electroporation, solid particle intrusion, lipofection, chemically-induced DNA uptake, microinjection or macroinjection. Viral infection can result in a multiplicity of nucleic acids functionally operative in the cell cytoplasm.

In general, recombinant immunoglobulins can be prepared by isolating DNA fragments corresponding to the heavy and light chain variable regions of a monoclonal antibody and joining them to each other by any one of the standard methods known to those of skill in the art and described by Molecular Cloning: A Laboratory Manual, Sambrook et al., eds., Cold Spring Harbor Laboratory, Cold Spring Harbor, N.Y. (1989). In one preferred embodiment, only DNA fragments corresponding to heavy chains are used to prepare suitable vectors for cell transformation. In one example of cell transformation, the recombinant DNA fragments can be inserted into Agrobacterium transfer vectors such that the genes of interest are inserted into the Agrobacterium genome. The recombinant Agrobacterium is then used to infect plant cells resulting in the production of the polypeptide of interest. In another example of cell transformation, the recombinant DNA fragments can be inserted into baculovirus transfer vectors such that the genes of interest are inserted into the viral genome in lieu of the baculovirus polyhedron gene. The recombinant virus is then used to infect insect cells resulting in the production of the polypeptide of interest.

An advantage of using insect cells that utilize recombinant baculoviruses for the production of IgBPs is that the baculovirus system allows production of mutant antibodies as well as combinatorial expression of immunoglobulin with other polypeptides (such as J chain) much more rapidly than stably transfected mammalian or plant cell lines. In addition, insect cells have been shown to correctly process and glycosylate eukaryotic proteins. Finally, the baculovirus expression of foreign protein has been shown to constitute as much as 50–75% of the total cellular protein late in viral infection, making this system an excellent means of producing milligram quantities of recombinant immunoglobulins.

The use of baculovirus *Autographica californica* nuclear polyhedron virus (AcNPV) and recombinant viral stocks in *Spodoptera frugiperda* (Sf9) cells to prepare large quantities of protein has been described by Smith et al., *Proc. Natl. Acad. Sci. U.S.A.* 82: 8404–8408, 1985, and Summers and Smith, *Bulletin B—Texas Agricultural Experiment Station*, May, 1987. A preferred method of preparing recombinant heavy chains covalently linked to J chain or the light chain constant region is through the expression of DNA encoding recombinant heavy chain, J chain, and light chain constant region via the baculoviral expression system in Sf9 insect cells.

Isolated DNA fragments that encode preferred genes are then inserted into the baculovirus transfer vectors. A preferred transfer vector is based on pAc360. The DNA fragments are digested, purified and ligated into unique restriction sites in the vector using standard techniques known to those of skill in the art and described by Molecular Cloning: A Laboratory Manual, Sambrook et al., eds., Cold Spring Harbor Laboratory, Cold Spring Harbor, N.Y. (1989).

Recombinant plasmid vectors are then co-transfected with linearized wild-type AcNPV into Sf9 cells. Cotransfection is preferentially accomplished using cationic liposomes, which are commercially available (e.g., from Invitrogen). Sf9 cells infected with occlusion-negative, recombinant viruses are then identified and can be grown in the desired quantity and under appropriate conditions such that large quantities of the desired binding protein are produced.

Methods for introducing polypeptide coding genes into mammalian cells have been described and are generally familiar to one skilled in the art. Such methods include, but are not limited to, liposome-mediated transformation, calcium phosphate transfection, electroporation, diethylamonioethyl dextran carrier and viral infection. It will be readily apparent that an optimal method of introducing genes into a particular eukaryotic cell species may not necessarily be the most effective for another species.

The advantage of using certain viruses for mammalian cell transformation is that a variety of mammalian cell lines are potential targets of viral infection. Recombinant Sindbis virus for example, allows rapid, high-level expression of heterologous proteins in mammalian cell lines as well as avian, reptilian, mosquito and Drosophila cells. The virus inhibits host protein synthesis allowing rapid identification and purification of the transgenic protein.

Isolated DNA fragments are introduced into a vector containing an appropriate polylinker site downstream from a promoter and upstream from a poly-A tail. A useful vector is pSinRep5 (Invitrogen). The recombinant vector is then linearized using appropriate restriction sites downstream from the poly-A tail. RNA transcripts are then produced (using, for example, the SP6 promoter) containing non-structural genes for in vivo replication of the recombinant RNA and the promoter and transgene of interest. The RNA is then used to transfect mammalian or other cells, such as baby hamster kidney (BHK) cells. Protein expression can be assayed 4–72 hours post infection. Alternatively, viral particles can be harvested and used for infection of another cell line.

In certain embodiments, an array comprises plants or cells transformed with polynucleotides encoding immunoglobulin heavy chains and immunoglobulin light chains, such that antibody molecules are produced. Within such arrays, individual immunoglobulin heavy and light chains produced by each plant or plant cell may associate with each other and assume a conformation having an antigen binding site specific for a preselected or predetermined antigen, as evidenced by its ability to be competitively inhibited. When the binding protein is an antigen binding protein, its affinity or avidity is generally greater than $10^5$ $M^{-1}$, preferably greater than $10^6$ $M^{-1}$, and more preferably greater than $10^8$ $M^{-1}$. Immunoglobulins for use in such embodiments may generally be derived from the B cells of an immunized host, each of which express a different IgBP.

Similarly, an IgBP array may comprise polynucleotides that encode portions of immunoglobulin heavy chains and portions of immunoglobulin light chains. The individual immunoglobulin heavy and light chain portions in each plant or plant cell may associate with each other and assume a conformation having an antigen binding site specific for a preselected or predetermined antigen. The antigen binding site on a Fab fragment has a binding affinity or avidity similar to the antigen binding site on an immunoglobulin molecule. Likewise, the antigen binding site on a SCAB protein has a binding affinity or avidity similar to the antigen binding site on an immunoglobulin molecule. Alternatively, an IgBP array may comprise polynucleotides that encode immunoglobulin heavy and light chain fragments that may associate within the plant cell to form Fv fragments with a biologically active conformation that has a binding site specific for a preselected or predetermined antigen. The antigen binding site on individual Fv fragments has an affinity or avidity for an antigen similar to the affinity displayed by the antigen binding site present on an immunoglobulin molecule.

Within certain preferred embodiments, IgBP arrays (preferably $C_HBP$ arrays) may be prepared in plants, plant cells and/or seeds. Such arrays may be prepared in any plant or plant cell that can be conveniently transformed. Suitable plant types include, but are not limited to, Arabidopsis, tobacco, Lemna (duckweed), corn, rice and Chlamydomonas. Techniques for transforming these and other plant types are well known in the art, and include Agrobacterium-mediated plant transformation, protoplast transformation, gene transfer into pollen, injection into reproductive organs, gene transfer using a plant cell infective virus or bacterium, mechanical disruption of plant cells containing no cell walls in the presence of DNA and solid particulates (e.g., glass beads), injection into immature embryos, acceleration into the plant cells on solid particles or fibers, or electroporation. As noted above, libraries of polynucleotides encoding more than one IgBP are used for transfection. Transfection may result in introduction of one or more polynucleotides into the nuclear genome of a plant cell. Alternatively, the introduced polynucleotide(s) may remain extrachromosomal after being introduced by viral infection. Preferably, the transfection technique results in a population of cells containing multiple functionally operative polynucleotides encoding IgBPs, or components thereof. Such techniques (that result in integration into the nuclear genome) include Agrobacterium-mediated transformation, biolistic transformation, direct DNA transfer, fiber-mediated transformation, microinjection, macroinjection and electroporation. Viral infection can result in multiple polynucleotides encoding IgBPs, or components thereof, functionally operative in the plant cell cytoplasm. It will be apparent that the selection of an optimal method for introducing genes will depend, in part, on the particular plant species.

The use of Agrobacterium-mediated expression vectors to introduce DNA into plant cells is well known in the art. See, for example, the methods described by Fraley et al., *Biotechnology* 3: 629, 1985 and Rogers et al., *Methods in Enzymology*, 153:253–277, 1987. Further, the integration of the Ti-DNA is a relatively precise process resulting in few rearrangements. The region of DNA to be transferred is defined by the border sequences and intervening DNA is usually inserted into the plant genome as described by Spielmann et al., *Mol. Gen. Genet.* 205:34, 1986 and Jorgensen et al., *Mol. Gen. Genet.* 207:471, 1987. Modern Agrobacterium transformation vectors are capable of replication in *Escherichia coli* as well as Agrobacterium, allowing for convenient manipulations, as described by Klee et al., in *Plant DNA Infectious Agents*, T. Hohn and J. Schell, eds., Springer-Verlag, New York (1985) pp. 179–203. Further recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology* 153:253, 1987, for example, have convenient multi-linker regions flanked by a promoter and a polyadenylation site for direct expression of inserted polypeptide coding genes, and are suitable for present purposes.

In those plant species where Agrobacterium-mediated transformation is efficient, this is the method of choice because of the facile and defined nature of the gene transfer (see Horsch et al., *Science* 227:1129–1231, 1985; Feldmann and Marks, Mol. Gen. Genet. 208:1–9, 1987; Chang et al., *Plant J.* 5:551–558, 1994; Bechtold et al., *Acad. Sci. Paris Science de la Vie* 316:1194–1199, 1993; Hansen and Chilton, *Curr Top Microbiol Immunol* 240:21–57, 1999). Few monocots appear to be natural hosts for Agrobacterium. However, transgenic plants may be produced in a variety of monocots using Agrobacterium vectors (as described, for example, by Bytebier et al., *Proc. Natl. Acad. Sci. U.S.A.* 84:5345, 1987; Hiei et al., *Plant J.* 6(2):271–282, 1994; Ishida et al., *Nat. Biotechnol.* 14(6):745–750, 1996; Hansen and Chilton, *Curr Top Microbiol Immunol* 240:21–57, 1999). Alternatively, vector-free or direct DNA transfer methods have been developed to transform a variety of plant species. As an example, transformation of plant protoplasts can be achieved using methods based on calcium phosphate precipitation, polyethylene glycol treatment, electroporation, microinjection, and combinations of these treatments. See, for example, Potrykus et al., *Mol. Gen. Genet.* 199:183, 1985; Lorz et al., *Mol. Gen. Genet.* 199: 178, 1985; Fromm et al., Nature 319:791, 1986; Uchimiya et al., *Mol. Gen. Genet.* 204:204, 1986; Callis et al., *Genes and Development* 1:1183, 1987; Marcotte et al., *Nature* 335:454, 1988; Roest and Gilissen, *Acta Bot Neerl* 38:1–23, 1989; Davey et al., *Plant Mol Biol* 13:273–285, 1989; Shimamoto et al., *Nature* 338:274–276, 1989; and Datta et al., *Bio/Technology* 8:736–740, 1990. Silicon carbide-mediated transformation may be used to generate stably transformed, fertile maize plants (Frame, et al., *The Plant Journal for Cell and Molecular Biology* 6:941–948, 1994) as well as tobacco cell cultures (Kaeppler, et al., Theoretical and Applied Genetics 84:560–566, 1992), *Agrostis alba* cell cultures (Asano et al., *Plant Cell Reports* 13:243–246, 1994), and *Chlamydomonas reinhardtii* (Dunahay, *BioTechniques* 15:452–460, 1993). Application of these systems to different plant species often depends upon the ability to regenerate that particular plant species from protoplasts or callus. Illustrative methods for the regeneration of cereals from protoplasts are described, for example, in Fujimura et al., *Plant Tissue Culture Letters* 2:74, 1985; Toriyama et al., *Theor Appl. Genet.* 73:16, 1986; Yamada et al., *Plant Cell Rep.* 4:85, 1986; Abdullah et al., *Biotechnology* 4:1087, 1986. Register et al., *Plant Mol. Bio.* 25(6):951–961, 1994; Blackhall N. W. et al., "Callus Initiation, Maintenance, and Shoot Induction in Rice," in Plant Cell Culture Protocols, Hall R. D. (editor), Humana Press (Totowa, N.J.), 1999, pgs. 19–30.

To transform plant species that cannot be successfully regenerated from protoplast or callus, other ways to introduce DNA into intact cells or tissues can be used. For example, regeneration of cereals from immature embryos or explants can be effected as described by Dasil, *Biotechnology* 6:397, 1988. In addition, "particle gun" or high-velocity microprojectile technology can be used. Using such technology, DNA is carried through the cell wall and into the cytoplasm on the surface of small (0.525 $\mu$m) metal particles that have been accelerated to speeds of one to several hundred meters per second (as described in Klein et al., *Nature* 327:70, 1987; Klein et al., *Proc. Natl. Acad. Sci. U.S.A.* 85:8502, 1988; and McCabe et al., *Biotechnology* 6:923, 1988). The metal particles penetrate through several layers of cells and thus allow the transformation of cells within tissue explants. Metal particles may be used to successfully transform corn cells and to produce fertile, stably transformed plants in a variety of species including model plants such as tobacco (Klein et al., 1988), as well as important crop species such as soybean (McCabe et al., 1988), maize (Fromm et al., *Bio/technology* 8: 833–839, 1990; Gordon-Kamm et al, *The Plant Cell* 2: 603–618 1990), rice (Christou et al., *Bio/technology* 9: 957–962, 1991), barley (Wan and Lemaux, Plant Physiology 104: 37–48, 1994) and wheat (Vasil et al., *Bio/technology* 10: 662–674, 1992; Weeks et al., *Plant Physiology* 102: 1077–1084, 1993). Transformation of tissue explants eliminates the need for passage through a protoplast stage and thus speeds the production of transgenic plants.

DNA can also be introduced into plants by direct DNA transfer into pollen, as described by Zhou et al., *Methods in Enzymology* 101:433, 1983; Hess, Intern Rev. Cytol. 107:367, 1987; Luo et al., *Plant Mol. Biol. Reporter* 6:165, 1988; and Saunders et al., *Molecular Biotechnology* 3:181–190, 1995. Expression of polypeptide coding genes can be obtained by injection of the DNA into reproductive organs of a plant as described by Pena et al., *Nature* 325:274, 1987. DNA can also be injected directly into the cells of immature embryos, followed by the rehydration of desiccated embryos as described by Neuhaus et al., *Theor. Appl. Genet.* 75:30, 1987; and Benbrook et al., in *Proceedings Bio. Expo.* 1986, Butterworth, Stoneham, Mass., pp. 27–54 (1986).

Regardless of the method of transformation, transformed plant cells are generally grown on a suitable medium. Cells may be grown on medium that does not promote differentiation (e.g., as calli), or may be grown such that plants are regenerated. For example, some lower plant species, such as Chlamydomonas, do not require regeneration and can express immunoglobulin binding proteins immediately after selection for the expression of a selectable marker, as a result of growth in an appropriate medium. Suitable media for a wide variety of plant cell types are well known to those of ordinary skill in the art. In general, transformed cells are selected based on expression of the selection marker, such that only those cells that contain at least one transfected polynucleotide encoding an immunoglobulin binding protein are permitted to grow.

Non-combinatorial arrays expressing heavy chain binding proteins may be generated using, for example, the MaxBac Baculovirus Expression System (Invitrogen). Briefly, insect cells are co-transfected with recombinant plasmid or plasmids and linearized Bac-and-Blue DNA. A viral supernatant fluid is harvested after the appropriate infection time and the virus is used to display recombinant plaques on agar plates using techniques recommended by the manufacturer. Individual plaques can then by used for the evaluation of binding protein expression. Alternatively, heavy chain binding protein arrays may be generated using the Sindbis Expression System (Invitrogen), allowing the expression of polypeptides in baby hamster kidney (BHK) cells and the production of viral particles that can be used to infect a variety of other eukaryotic cell lines.

The regeneration of plants from either single plant protoplasts or various explants is well known in the art. See, for example, Methods for Plant Molecular Biology, A. Weissbach and H. Weissbach, eds., Academic Press, Inc. (San Diego, Calif.; 1988). This regeneration and growth process includes the steps of selection of transformant cells and shoots, rooting the transformant shoots and growth of the plantlets in soil.

The regeneration of plants containing the foreign gene introduced by *Agrobacterium tumefasciens* from leaf explants can be achieved as described by Horsch et al., *Science* 227:1229–1231, 1985. In this procedure, transformants are grown in the presence of a selection agent and in a medium that induces the regeneration of shoots in the plant species being transformed, as described by Fraley et al., *Proc. Natl. Acad. Sci. U.S.A.* 80:4803, 1983. This procedure typically produces shoots within two to four weeks, and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, such variations being well known in the art.

An array may consist of a set of seeds generated from transformed plants. While such seeds have the potential to germinate into plants that express IgBPs, expression does not generally occur when the seeds are dormant (although some expression may occur during seed development). Nonetheless, such a set of seeds is considered an array.

Within arrays, the IgBPs or components thereof may be secreted from cells or may accumulate in one or more intracellular compartments. Secreted proteins may or may not be contained by a cell wall. For example, the CW15 mutant of Chlamydomonas does not express a cell wall and IgBPs containing leader sequences are secreted directly into the growth medium. In this instance, the desired IgBP can be identified by assaying a portion of the growth medium for the desired characteristic. In higher plants, secreted IgBPs are generally contained by the cell wall and may accumulate in the apoplastic water. A desired IgBP can be assayed after disruption of the cell wall using any of a variety of standard mechanical techniques (e.g., mortar and pestle homogenization).

Within certain embodiments, an array of IgBPs in plant cells is derived from a progeny population of plant cells (i.e., plant cells resulting from the sexual cross of transformants expressing IgBP components). In such an array, some or all of the progeny population contain polynucleotides encoding IgBP components, such that functional IgBPs are expressed in the array. In such arrays, useful IgBP component polynucleotides include those that encode a second polypeptide that can autogenously associate with a first polypeptide in such a way as to form a biologically functional IgBP. Examples of such IgBP components are heavy and light chains of antibodies.

The sexual cross of different members of a plant species has been well described by Mendel in 1865 (an English translation of Mendel's original paper together with comments and a bibliography of Mendel by others can be found in Experiments In Plant Hybridization, Edinburgh, Scotland, Oliver Boyd, eds., 1965). When the plants are flowering plants, the sexual cross involves contacting viable pollen from one population of plants with the stigma of another population of plants of a sexually compatible species. When the plant cells are photosynthetic unicellular organisms (e.g. Chlamydomonas), the sexual cross involves fusion of cells of +and − mating types, followed by meiosis and tetrad formation. Progeny from sexual crosses can comprise seeds or tetrads.

Progeny resulting from a sexual cross of transformed plant cells may, within certain embodiments, be resolved into an array in which some or all of the progeny contain polynucleotides encoding a single IgBP. Briefly, transformed plant cells expressing polynucleotides encoding multiple IgBPs can be sexually crossed to produce a progeny population. For higher plants, the sexual cross involves pollination as described above. The source of pollen can be either the same plant (self pollination) or a different plant (cross pollination). In some cases pollination is not required for seed development. The resulting progeny population contains the genetic segregation events of the polynucleotides encoding various IgBPs or components. Some of the progeny may contain polynucleotides encoding a single IgBP.

For haploid organisms such as Chlamydomonas, resolution of multiple binding events may also be accomplished by molecular genetic techniques. Nucleic acids encoding IgBPs can be identified by Southern blotting and isolated by PCR using known primers. The isolated nucleic acids can then be used for re-transformation of the haploid plant cell to produce a secondary array representing the resolved nucleic acids encoding IgBPs. In this process, vector DNA encoding IgBPs is amplified using oligonucleotides complementary to the boundary regions of the expression cassette. The amplified DNA is ideally suitable for ligation into an expression vector for re-transformations of a new population of Chlamydomonas cells. Transformants from this population contain relatively few different IgBPs and therefore there is a higher probability of generating a population of transformed cells wherein each nucleic acid is expressed uniquely by an individual transformed cell.

Immunoglobulin Binding Protein Array Compositions

The present invention also provides compositions that comprise an array of encapsulated IgBPs. IgBPs may be encapsulated, for example, within plant cells, plant cell walls, enteric coatings, coatings and the like. Particularly preferred are compositions containing no more than 10,000 grams of plant material for each 100 nanograms of IgBP. Such compositions typically contain at least 100 nanograms of plant material for each 10 grams of IgBP. In more preferred embodiments, a composition comprises no more than 10,000 grams of plant material for each milligram of IgBP, but at least 100 nanograms of plant material for each gram of IgBP and more preferably at least one milligram of plant material for each 500 milligrams of IgBP.

A composition may further comprise substances such as chlorophyll, synergistic compounds, medicines, compounds derived from medicinal plants and/or various pharmaceuticals.

Assays for Screening Arrays of Immunoglobulin Binding Proteins

Transgenic arrays as provided herein are useful for the discovery of IgBPs having desired characteristics. From the transgenic arrays provided herein, individual eukaryotic organisms or clones of eukaryotic cells can be identified rapidly, enabling the easy access to an economical, high yield process for the large scale production of a desired IgBP.

As noted above, plants are a particularly preferred host organism for the transgenic arrays described herein. When a sexual cross is performed between two populations of plant cells, each expressing IgBPs or components of IgBPs, some or all of the progeny can express functional IgBPs that comprise multiple IgBP components. Such progeny may be of particular use within functional screens for IgBPs having multiple polypeptide subunits.

More specifically, once regenerated plants are adapted to growth in soil, small sections of leaf can be removed to assay for the presence of IgBPs. Alternatively, the plants can be allowed to set seed by either self-pollination or cross pollination and the assays for expression of IgBPs can be performed on individual seeds or portions of seeds. When the transformants are individual cells (e.g., Chlamydomonas) the cells may be grown in solid or liquid medium to obtain a sufficient quantity for performing assays. Assays can be immunological (e.g., ELISA) or functional. Functional assays may involve, for example, binding of the IgBP to cognate factors immobilized on a solid support. When the IgBP is an antibody, the cognate factor is an antigen. Assays for determining the number of copies of IgBP as well as the number of different IgBPs being expressed in the primary transformants include Southern blotting and DNA sequencing of cloned cDNAs derived from cellular RNA. Description of these assays may be found in Antibodies: A Laboratory Manual, Harlow and Lane, eds., Cold Spring Harbor, N.Y. (1988) and Molecular Cloning: A Laboratory Manual, Sambrook et al., eds., Cold Spring Harbor Laboratory, Cold Spring Harbor, N.Y. (1989).

The following Examples are offered by way of illustration and not by way of limitation.

EXAMPLES

Example 1

Isolation and Expression in Maize of Immunoglobulin Heavy Chain-Coding Genes and Immunoglobulin Light Chain-Coding Genes Derived From B Cells in Bone Marrow This Example illustrates the preparation of representative immunoglobulin binding protein components for use in preparing an array of immunoglobulin binding proteins in plant cells.

Bone marrow (~$10^7$ cells) was obtained from donors at local hospitals. Donors were chosen on the basis of (a) having had *Clostridium difficile*-associated diarrhea within the previous two months and (b) having toxin neutralizing antibodies in their serum. Bone marrow was obtained from the subset of this population whose diarrhea resolved without the intervention of any further antibiotic therapy.

Bone marrow cells were washed multiple times in cold PBS then incubated with combined FITC-labeled *Clostridium difficile* toxin A and toxin B. This procedure was used to identify B cells expressing anti-toxin A or anti-toxin B on their cell surfaces. The *Clostridium difficile* toxins were prepared from cultures of *Clostridium difficile* as described by Lyerly et al., *Infect Immun* 35:1147–50, 1982.

Fluorescent labeling of the toxins was by reaction with fluorescein isothiocyanate (FITC) using procedures provided by the manufacturer (Pierce). Incubation of bone marrow cells with the combined FITC-labeled *Clostridium difficile* toxin A and toxin B was by the procedures described in Hoven et al., *J. Immunol. Methods* 117:2275–84, 1989. The tagged cells were shown to be B cells by double staining with phycoerythrin-conjugated anti-human Ig.

Total RNA from the selected bone marrow cells was prepared using the QIAamp RNA Blood Mini-Kit system (Qiagen) according to the instructions provided.

PCR amplification of the isolated RNA employed oligonucleotides complementary to conserved 3' and 5' regions of immunoglobulin (IgG 1) transcripts as previously described in Antibody Engineering, Carl A, Borrebaeck, Ed., W. H. Freeman and Company, New York, N.Y., 1995. The oligonucleotide primers introduced unique restriction sites at each end of the amplified polynucleotide to allow for ligation into a plant expression vector. The amplified portion of the immunoglobulin polynucleotides extended from the 5' end encoding the respective FRI regions to the 3' end encoding the stop codon. In addition, appropriate 5' and 3' restriction sites were introduced in the process of amplification. The amplified heavy and light polynucleotide chains therefore corresponded to the first six codons at the 5' end of the RNAs and the last six codons of the constant regions with the restriction sites introduced outside of the respective terminal codons. This immunoglobulin binding protein array consisting of double stranded amplified cDNAs from the sorted cells was prepared for insertion into a plant expression vector, by converting the ends of the double stranded cDNA to the appropriate sticky ends for ligation into the vector (Molecular Cloning: A Laboratory Manual, Sambrook et al., eds., Cold Spring Harbor Laboratory, Cold Spring Harbor, N.Y. 1989) by digestion with a restriction endonuclease according to the manufacturer's protocol (New England BioLabs).

The vector allowed for the expression of both heavy and light chains using the ubiquitin promoter and nopaline synthase terminator as described by Ishida et al., *Nature Biotechnology* 14:745–750, 1996 and Register et al., *Plant Mol Biol* 25:951–961, 1994.

The vector further contained polynucleotides encoding signal sequences (MDWTGRFLFVVAAATGVQS; SEQ ID NO: 73) upstream from each site for insertion of the amplified immunoglobulins. The signal sequence was derived from the Kabat database (Kabat et al., Sequences of Immunological Interest, National Institutes of Health, Bethesda, Md., 1991) to allow for association of both heavy and light chain nascent polypeptides with the endomembrane system of the plant cell. In addition, the vector contained a multiple cloning site immediately downstream from the signal sequence encoding regions. The amplified regions were then ligated into the vector to encode a heavy chain polynucleotide consisting of a signal sequence, a diversity of variable region and the entire gamma constant region; and a light chain polynucleotide consisting of a signal sequence, a diversity of light chain variable region and the entire kappa constant region.

The recombinant population of vectors was then used to transform *Agrobacterium tumefasciens* as described by Ishida et al., *Nature Biotechnology* 14:745–75, 1996. The transformed Agrobacterium was then used to infect immature corn embryos followed by selection and regeneration of maize plants as described in Ishida et al. The resulting array of plant cells producing IgBP polypeptides (i.e., IgBPs and/or IgBP components) comprised approximately 1000 plants.

To locate the position in the array of various IgBP polypeptides, samples of leaf tissue were taken from each plant. A variety of assays were performed to characterize the presence of IgBPs, the functionality of IgBPs, and the variety of IgBP components in each transformant. IgBP components (gamma chains or kappa chains) were detected by ELISA in 96 well plates. In one set of plates the capture of IgBP components was by reaction with immobilized goat anti-human kappa chain antibody and the detection was by horse radish peroxidase conjugated goat anti-human kappa chain antibody. In another set of plates the capture of IgBP components was by reaction with immobilized goat anti-human gamma chain antibody and the detection was by horse radish peroxidase conjugated goat anti-human gamma chain antibody. In a third set of plates the capture of IgBP components was by reaction with immobilized goat anti-human gamma chain antibody and the detection was by horseradish peroxidase-conjugated goat anti-human kappa chain antibody. Detection of captured IgBP components was by the procedures previously described (Antibodies: A Laboratory Manual, Harlow and Lane, eds., Cold Spring Harbor, N.Y., 1988). The results demonstrated that the majority of plants co-expressed gamma and kappa chains.

The leaf material was further evaluated for the ability of the expressed IgBPs to bind the toxin A or toxin B proteins. In these assays, ELISA plates were coated with either toxin A or B to capture the IgBPs. The ELISA procedures generally followed those previously described (Hiatt et al., *Nature* 342:76–78, 1989). Leaf extracts were incubated in the ELISA wells to allow reaction of potential immunoglobulin binding proteins with the immobilized toxins. Screening the entire array of approximately 1000 plants as described above identified 10 plants expressing functional anti-toxin A antibodies and 5 plants expressing functional anti-toxin B antibodies. From these results, it appears that greater than 20% of the total polynucleotide population encoded anti-toxin A heavy or light chains. Similarly, greater than 14% of the total population encoded anti-toxin B heavy or light chains. The remaining 66% of the polynucleotides derived from the sorted cells may have encoded unrelated immunoglobulins.

To assess the variety of immunoglobulin binding protein components contained in those plants that expressed functional anti-toxins, PCR amplification of gamma or kappa transcripts were cloned into bacterial transformation vectors as described (Antibody Engineering, Carl A, Borrebaeck, Ed., W. H. Freeman and Company, New York, N.Y., 1995). Plasmids derived from each of the bacterial colonies were then subjected to automated DNA sequencing as described (DNA Sequencing: From Experimental Methods to Bioinformatics, L. Alphey, Bios Scientific Publishers, Oxford, England, 1997). The sequences derived from various plants revealed that in some cases more than one set of IgBP components was expressed in a single transformant.

To segregate the different polynucleotides encoding different IgBPs into different progeny plants, the transformants expressing multiple IgBP polypeptides were self-pollinated to produce seed sets. The resulting array of seeds was grown into individual plantlets, at which time portions of the leaf were removed to assay for the presence of functional IgBPs as described above. Since the heavy and light chains were co-expressed on the same vector, the genetic segregation potentially identifies functional anti-toxin heavy and light chains expressed from the same vector. This is useful since the parental plants expressing anti-toxins could have formed antibody from heavy and light chains polynucleotides on different vectors co-integrated into the same nucleus during Agrobacterium transformation. Of the 15 plants expressing anti-toxin antibodies, 14 produced a progeny array where some members of the array expressed anti-toxin antibodies indicating co-expression of heavy and light chains from the same vector. The single parental plant that produced progeny containing no anti-toxin antibodies presumably expressed anti-toxin heavy and light chain polynucleotides from different vectors, which co-integrated during transformation but which segregated in the progeny. This observation is consistent with the known ability of Agrobacterium to introduce more than one vector into a nucleus during transformation.

Example 2

Isolation and Expression in Maize of Immunoglobulin Heavy Chain-Coding Genes and J Chain-Coding Gene This Example illustrates the preparation of representative immunoglobulin heavy chain binding protein components for use in generating an array of immunoglobulin heavy chain binding proteins in plant cells.

RNA was prepared as described in Example 1. PCR amplification of the isolated RNA employed oligonucleotides complementary to conserved 3' and 5' regions of the variable region of the immunoglobulin heavy chain (IgGI) transcripts as previously described in Antibody Engineering, Carl A, Borrebaeck, Ed., W. H. Freeman and Company, New York, N.Y., 1995. The oligonucleotide primers introduced unique restriction sites at each end of the amplified polynucleotide to allow for ligation into a plant expression vector. The amplified portion of the immunoglobulin polynucleotides extended from the 5' end encoding the respective FRI regions to the 3' end encoding the first six amino acids of the CH1 region. In addition, appropriate 5' and 3' restriction sites were introduced in the process of amplification. The amplified heavy chain polynucleotide chains therefore corresponded to the first six codons at the 5' end of the RNAs and the first six codons of the constant regions with the restriction sites introduced outside of the respective terminal codons. This immunoglobulin heavy chain binding protein array consisting of double stranded amplified cDNAs from the sorted cells was prepared for insertion into a plant expression vector, by converting the ends of the double stranded cDNA to the appropriate sticky ends for ligation into the vector (Molecular Cloning: A Laboratory Manual, Sambrook et al., eds., Cold Spring Harbor Laboratory, Cold Spring Harbor, N.Y. 1989) by digestion with a restriction endonuclease according to the manufacturer's protocol (New England BioLabs). Synthetic polynucleotides encoding J chain were additionally prepared for ligation into the plant vector by PCR amplification as above. Finally, the constant region of an IgG-A hybrid heavy chain (Ma et al., *Science* 268:716–719) was amplified by PCR to contain appropriate restriction sites for ligation into the plant vector downstream from the variable region amplified above.

As in Example 1, the vector allowed for the expression of two open reading frames using two ubiquitin promoters and nopaline synthase terminator as described by Ishida et al., *Nature Biotechnology* 14:745–750, 1996 and Register et al., *Plant Mol Biol* 25:951–961, 1994.

The vector further contained a polynucleotide encoding signal sequences (MDWTGRFLFVVAAATGVQS; SEQ ID NO: 73) upstream from the site for insertion of amplified DNAs and downstream from the first promoter. The signal sequence was derived from the Kabat database (Kabat et al., Sequences of Immunological Interest, National Institutes of Health, Bethesda, Md., 1991) to allow for association of heavy chain nascent polypeptides with the endomembrane system of the plant cell. In addition, the vector contained a multiple cloning site immediately downstream from the signal sequence codons at the first promoter site and immediately downstream from the second promoter site. The amplified heavy chain constant region was first ligated into the vector downstream from the signal sequence at the first promoter site. The remaining restriction sites located between the signal sequence and the heavy chain constant region were used for ligation of the amplified heavy chain variable regions prepared above. The amplified J chain (containing a signal sequence) was ligated downstream from the second promoter. The resulting vector encoded a heavy chain polynucleotide consisting of a signal sequence, a diversity of variable regions and the entire gamma-alpha hybrid constant region (Ma et al., Science 268:716–719); and a J chain polynucleotide containing a signal sequence.

The recombinant population of vectors was then used to transform *Agrobacterium tumefasciens* as described above. Regenerated leaf material was evaluated as described above with the exception that in one set of ELISA plates both the capture and detection antibody recognized human alpha constant regions. In another set of ELISA plates capture was with anti-alpha antibodies and detection was with anti-J chain antibodies. Evaluation of binding to toxin A or toxin B was performed as described above where leaf extracts were incubated in the ELISA wells to allow reaction of potential heavy chain binding proteins with the immobilized toxins. Screening the entire array of approximately 1000 plants as described above identified 50 plants expressing functional binders of toxin A and 40 plants expressing functional binders of toxin B. From these results, it appears that the non-combinatorial approach to isolating binding proteins containing no light chain variable regions yields a higher proportion of transformation events expressing binding proteins compared to the combinatorial approach involving the random pairing of heavy and light chains. The ability to detect these binding proteins appears to be due to their assembly into a polymeric molecular structure with enhanced avidity for the toxins.

Example 3

Preparation of an Array of Functional Immunoglobulin Binding Proteins from Binding Protein Components by a Sexual Cross of Higher Plants This Example illustrates the generation of an array of plants that express functional immunoglobulin binding proteins from plant populations that express different immunoglobulin binding protein components.

cDNAs encoding heavy and light chains derived from the B cell populations described above were cloned separately into vectors allowing for expression of heavy chains and light chains in different plant populations. The procedures described above were performed to generate plant transformants expressing arrays of heavy chains or light chains (immunoglobulin binding protein components). In order to form an array of immunoglobulin binding proteins, pollen from the light chain transformants was used to pollinate the heavy chain transformants to produce a seed set. The seeds were then grown into individual plantlets and subjected to the analysis for identification of immunoglobulin binding proteins described above. Results similar to Example 1 were obtained indicating that the random assortment of heavy and light chains by cloning them into different vectors followed by assembly upon crossing plants is comparable to cloning heavy and light chains into the same vector followed by assembly in primary transformants.

Example 4

Immunoglobulin Binding Protein Array in *Chlamydomonas reinhardtii*

This Example illustrates the preparation of an immunoglobulin binding protein array in *Chlamydomonas reinhardtii.*

A. Transformation Techniques.

Cells were transformed using the glass bead protocol as previously described (Kindle, *Proc. Natl. Acad. Sci. USA* 87:1228–1232, 1990). The transformation procedure described below uses the argininosuccinate lyase (ARG7, Debuchy et al., *EMBO J.* 8:2803–2809, 1989) as the selectable marker gene and transformants are selected as arginine prototrophs on medium not supplemented with arginine. Cells ($arg^-$, CW-15 strain, lacking a cell wall) were first grown under constant high light to mid-log phase in non-selective medium. About $5\times10^7$ cells were resuspended in 300 $\mu$l of medium, 150 $\mu$l 20% PEG-8000 (5% final concentration) and 0.3 g of acid-washed, heat-sterilized glass beads were then added. Ten $\mu$g of test plasmid DNA, along with 10 $\mu$g of pARG7.8 DNA (plasmid DNA containing ARG7), was added to the cells and the mixture was then agitated for 10 seconds with a vortex mixer at the highest setting. Alternatively, 5 mg of heat-sterilized silicon carbide whiskers was used and vortexed for 90 seconds (Dunahay, *BioTechniques* 15:452–460, 1993). The transformation mixture was then spread onto selective agar plates. Plates were placed under light and colonies were visible to the naked eyes after 7–10 days. All plasmid DNA used was linearized prior to use. A transformation with pARG7.8 DNA alone was always included as a control.

B. Expression of an Immunoglobulin Binding Protein Array.

The IgG array isolated by PCR from the B cells selected above (anti-toxin A and B) were introduced into bacterial vectors (pBluescript). These vectors were used to transform bacteria and generate a library of polynucleotides encoding immunoglobulin binding protein components (gamma and kappa chains). The sequences of the variable regions of 100 polynucleotides (50 gamma chains and 50 kappa chains) was determined by automated sequence analysis. Variable regions of each of these polynucleotides were synthesized to reflect the codon bias of Chlamydomonas. The synthesis strategy introduced unique Sac and Xho restriction sites at the ends of each DNA. Likewise, a single kappa constant region and gamma constant region (sequence derived from Kabat et al.) were synthesized with Chlamydomonas codon bias. The synthetic kappa and gamma constant region DNAs were first restricted and ligated into separate Xho-EcoR1 restricted pBluescript vectors to create separate vectors containing synthetic immunoglobulin constant region polynucleotides. These vectors were cloned and purified and were then used as the recipients for Sac-Xho restricted synthetic variable region DNAs to create an array of separate gamma and kappa polynucleotides encoding the diverse variable regions and constant regions of full length gamma and kappa-encoding polynucleotides. These vectors were used to transform bacteria from which plasmids were purified and automated sequence analysis was used to identify the original 100 variable regions comprising the arrays. These plasmids were mixed and the Sac-EcoR1 restriction fragments were subcloned into the pARG7 vector. The pARG7 vector contained a signal sequence derived from the Kabat database (MDWTGRFLFVVAAATGVQS; SEQ ID NO: 73) upstream from Sac-EcoR1 sites. The ligation product created full length heavy and light chain polynucleotides capable of co-expression with a signal sequence to direct polypeptide synthesis to the endomembrane system of the cell. Colonies on agar plates were tested for expression of antibodies using a nitrocellulose lift assay. Nitrocellulose circles were placed on the agar plates containing colonies on order to adsorb sufficient antibody onto the paper to allow for functional detection.

Example 5

Expression of Heavy Chain Binding Protein Genes in Insect Cells

This example illustrates the generation of an array of insect cells that express functional heavy chain binding proteins.

The heavy chain and J chain PCR products derived from B cells as described above were additionally manipulated to allow for expression in insect cells. In general, the double stranded cDNA from the selected B cells described above was prepared for insertion into an insect expression vector, by converting the ends of the double stranded cDNA to the appropriate sticky ends for ligation into the vector (Molecular Cloning: A Laboratory Manual, Sambrook et al., eds., Cold Spring Harbor Laboratory, Cold Spring Harbor, N.Y. 1989) by digestion with a restriction endonuclease according to the manufacturer's protocol (New England Biolabs). The vector (p2Bac, Invitrogen) allowed for the expression of both heavy and J chains using the $P_{P10}$ and the $P_{PH}$ promoters respectively and appropriate polyadenylation sequences (BGH and PH respectively, Invitrogen). The vector therefore was potentially capable of co-expression of both a heavy chain and a J chain. The vector further contained a polynucleotide encoding a signal sequence derived from the Kabat database (Kabat et al., Sequences of Immunological Interest, National Institutes of Health, Bethesda, Md., 1991) to allow for association of both heavy and J chain nascent polypeptides with the endomembrane system of the insect cell. The signal sequence was located immediately upstream from the first polylinker which contained convenient restriction sites for introduction of additional heavy chain elements. Downstream from the first polylinker, polynucleotides encoding the constant region of the human mu heavy chain were inserted. The mu heavy chain region obtained by amplification by PCR, corresponded to codons encoding the last five amino acids and stop codon at the 3' end of the RNA, as well as the first six codons of the constant region. The heavy chain V region DNA, encoding the heavy chain portion of the combining sites recognizing toxins A or B, was ligated into the first polylinker sight after introduction of the signal and constant region elements. Polynucleotides encoding the entire J chain including signal sequence containing appropriate restricted 3' and 5' ends to allow ligation into the second polylinker site were introduced into the vector last. The vector consequently encoded a heavy chain polynucleotide consisting of a signal sequence, a variable region and an mu constant region; and a J chain polynucleotide consisting of a signal sequence and the entire coding region of a human J chain. An additional vector was constructed which encoded the constant region of the human kappa light chain downstream from a unique promoter ($P_{PH}$ in pMelBac A, Invitrogen) and an insect signal sequence.

The resulting recombinant vectors as well as linearized AcNPV BV DNA (Pharmingen) were used to co-infect Sf insect cells using procedures recommended by the manufacturer to generate an array of viral plaques on agar plates. Each plaque potentially contained the virions encoding unique heavy chain binding proteins as well as the unique heavy chain binding proteins themselves. Virus particles from approximately 1000 of the plaques were used to infect High Five™ insect cells (Invitrogen) in an array of 96 well plates (~$10^6$ cells per well). 72 hours post-infection cells and supernatant were harvested, brought to 1 mL total volume, and 10–100 µL were analyzed for composition and functionality. Identification of desired heavy chain and binding functionality can utilize any of a variety of techniques known to those of skill in the art such as ELISA, immunoblotting, Western blotting, immunoprecipitation and such, all of which are described in Harlow and Lane, "Using Antibodies: A Laboratory Manual", Cold Spring Harbor Press, Cold Spring Harbor, N.Y., 1999.

Analysis of the antigen binding capability of each supernatant by ELISA identified a population of heavy chain binding proteins recognizing either toxin A or toxin B. Approximately 5% of the wells containing transformed insect cells expressed detectible binding proteins recognizing toxin A and 3% expressed binding proteins recognizing toxin B. These results are similar to those of Example 2.

Example 6

Expression of Heavy Chain Binding Protein Genes in Mammalian Cells

This example illustrates the generation of an array of mammalian cells that express functional heavy chain binding proteins.

The heavy chain and J chain PCR products derived from B cells as described above were additionally manipulated to allow for expression in baby hamster kidney (BHK) cells. In general, the double stranded cDNAs from the selected B cells described in Example 1 was engineered to be expressed as human mu isotypes as described in Example 6 and was further prepared for insertion into the Sindbis expression vector, using methods describe above. The vector (pSinRep5, Invitrogen) was therefore engineered to allowed for the expression of heavy and J chains using $P_{SG}$ promoters and appropriate polyadenylation sequences. The vector therefore was potentially capable of co-expression of both a heavy chain and a J chain.

The vector population was digested with an appropriate restriction enzyme. The resulting recombinant linearized vectors were used to generate capped RNA transcripts using the Sindbis Expression System kit. The transcripts were then used to infect BHK cells. The supernatant medium from the infected cells containing recombinant virus particles was then used to identify the expressed heavy chain binding proteins. Identification of desired heavy chain binding proteins used the techniques described above.

Analysis of the antigen binding capability of each supernatant by ELISA identified a population of heavy chain binding proteins recognizing either toxin A or toxin B. Approximately 4% of the wells containing transformed BHK cells expressed detectible binding proteins recognizing toxin A and 3% expressed binding proteins recognizing toxin B. These results are similar to those of Example 2.

From the foregoing, it will be appreciated that, although specific embodiments of the invention have been described herein for the purpose of illustration, various modifications may be made without deviating from the spirit and scope of the invention.

What is claimed is:

1. A method for preparing a plant heavy chain binding protein $C_H$BP array, comprising the steps of:

(a) transforming a population of plant cells with a library of at least two different polynucleotides, wherein each polynucleotide encodes a different $C_H$BP component that forms at least one disulfide bond with at least one polypeptide in the transformed cell to generate a $C_H$BP that specifically binds to a ligand with a $K_D<10^{-6}$ moles/liter, wherein each component;

(i) comprises an amino acid sequence that is substantially identical to a constant region tailpiece of a mu or alpha chain of a native immunoglobulin heavy chain; and (ii) comprises a combining site comprising an amino acid sequence;

(1) substantially identical to a 25 consecutive amino acid portion of an immunoglobulin light chain variable region; or (2) substantially identical to a 25 consecutive amino acid portion of an immunoglobulin heavy chain variable region;

(b) transforming the population of cells from step (a) with a J chain polypeptide;

(c) growing the transformed plant cells on a growth medium to form plants; and (d) sexually crossing the plants to generate progeny, such that the progeny comprise polynucleotides encoding $C_H$BP components disulfide linked by a J chain and sufficient to form a functional $C_H$BP that comprises at least four combining sites;

and therefrom preparing a plant $C_H$BP array.

2. A method according to claim 1, wherein the progeny are seeds.

3. A method according to claim 1, wherein the library comprises at least 10 different polynucleotides.

4. A method according to claim 1, wherein the library comprises at least 100 different polynucleotides.

5. A method according to claim 1, wherein the library comprises at least 1000 different polynucleotides.

6. A method according to claim 1, wherein the library comprises at least 10,000 different polynucleotides.

7. A method according to claim 1, wherein the step of transforming is performed via Agrobacterium-mediated transformation, chemically-induced DNA uptake, electroporation, solid particle intrusion, biolistics, microinjection, macroinjection, lipofection or viral infection.

8. A method according claim 1, wherein the binding proteins accumulate in an intracellular compartment of the cells.

9. A method according to claim 1, wherein the binding proteins are secreted from the cells.

10. A method according to claim 1, wherein the plant cells are dicotyledonous plant cells.

11. A method according to claim 10, wherein the plant cells are tobacco or Arabidopsis plant cells.

12. A method according to claim 1, wherein the plant cells are monocotyledonous plant cells.

13. A method according to claim 12, wherein the plant cells are corn, Lemna or rice plant cells.

14. A method according to claim 1, wherein the plant cells are lower plant cells.

15. A method according to claim 14, wherein the plant cells are green algae calls.

16. A method according claim 15, wherein the plant cells are *Chlamydomonas rheinhardtii*.

17. A method according to claim 1 wherein each CHBP component comprises a variable region from a light chain.

18. A method according to claim 1 wherein each CHBP component comprises a variable region from a heavy chain.

* * * * *

UNITED STATES PATENT AND TRADEMARK OFFICE
CERTIFICATE OF CORRECTION

PATENT NO.     : 6,696,620 B2                                    Page 1 of 1
DATED          : February 24, 2004
INVENTOR(S)    : Andrew C. Hiatt and Mich B. Hein It is certified that error appears in the above-identified patent and that said Letters Patent is hereby corrected as shown below:

<u>Column 94,</u>
Line 10, replace "calls" with -- cells --.

Signed and Sealed this

Twenty-fifth Day of May, 2004

JON W. DUDAS
*Acting Director of the United States Patent and Trademark Office*

SEQUENCE LISTING

<160> NUMBER OF SEQ ID NOS: 182

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)
<223> OTHER INFORMATION: Any amino acid

<400> SEQUENCE: 1

Phe Gly Xaa Gly
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)..(4)
<223> OTHER INFORMATION: Any amino acid

<400> SEQUENCE: 2

Cys Xaa Xaa Xaa
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 3

Leu Glu Trp Ile Gly
  1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)
<223> OTHER INFORMATION: Any amino acid

<400> SEQUENCE: 4

Trp Gly Xaa Gly
  1

<210> SEQ ID NO 5
<211> LENGTH: 14
<212> TYPE: PRT
<213> ORGANISM: Homo sapiens

<400> SEQUENCE: 5

Arg Ala Ser Gln Ser Leu Val Ser Ile Ser Ser Tyr Leu Ala
 1               5                   10

<210> SEQ ID NO 6
<211> LENGTH: 7
<212> TYPE: PRT
<213> ORGANISM: Homo sapiens

<400> SEQUENCE: 6

Ala Ala Ser Ser Leu Glu Ser
 1               5

<210> SEQ ID NO 7
<211> LENGTH: 10
<212> TYPE: PRT
<213> ORGANISM: Homo sapiens

<400> SEQUENCE: 7

Gln Gln Tyr Asn Ser Leu Pro Glu Trp Thr
 1               5                   10

<210> SEQ ID NO 8
<211> LENGTH: 16
<212> TYPE: PRT
<213> ORGANISM: Homo sapiens

<400> SEQUENCE: 8

Arg Ser Ser Gln Ser Leu Leu His Ser Asp Gly Asp Thr Tyr Leu Asn
 1               5                   10                  15

<210> SEQ ID NO 9
<211> LENGTH: 7
<212> TYPE: PRT
<213> ORGANISM: Homo sapiens

<400> SEQUENCE: 9

Leu Val Ser Asn Arg Ala Ser
 1               5

<210> SEQ ID NO 10
<211> LENGTH: 8
<212> TYPE: PRT
<213> ORGANISM: Homo sapiens

<400> SEQUENCE: 10

Met Gln Ala Leu Gln Pro Arg Thr
 1               5

<210> SEQ ID NO 11
<211> LENGTH: 12
<212> TYPE: PRT
<213> ORGANISM: Homo sapiens

<400> SEQUENCE: 11

Arg Ala Ser Gln Ser Val Ser Ser Ser Tyr Leu Ala
 1               5                   10

<210> SEQ ID NO 12
<211> LENGTH: 7
<212> TYPE: PRT
<213> ORGANISM: Homo sapiens

<400> SEQUENCE: 12

Gly Ala Ser Ser Arg Ala Thr

-continued

<210> SEQ ID NO 13
<211> LENGTH: 10
<212> TYPE: PRT
<213> ORGANISM: Homo sapiens

<400> SEQUENCE: 13

Gln Gln Tyr Gly Ser Ser Pro Pro Leu Thr
 1               5                  10

<210> SEQ ID NO 14
<211> LENGTH: 17
<212> TYPE: PRT
<213> ORGANISM: Homo sapiens

<400> SEQUENCE: 14

Lys Ser Ser Gln Ser Val Leu Tyr Ser Ser Asn Asn Lys Asn Tyr Leu
 1               5                  10                  15

Ala

<210> SEQ ID NO 15
<211> LENGTH: 7
<212> TYPE: PRT
<213> ORGANISM: Homo sapiens

<400> SEQUENCE: 15

Trp Ala Ser Thr Arg Glu Ser
 1               5

<210> SEQ ID NO 16
<211> LENGTH: 8
<212> TYPE: PRT
<213> ORGANISM: Homo sapiens

<400> SEQUENCE: 16

Gln Gln Tyr Tyr Ser Thr Pro Thr
 1               5

<210> SEQ ID NO 17
<211> LENGTH: 14
<212> TYPE: PRT
<213> ORGANISM: Homo sapiens

<400> SEQUENCE: 17

Ser Gly Ser Ser Ser Asn Ile Ile Gly Asn Asn Tyr Val Ser
 1               5                  10

<210> SEQ ID NO 18
<211> LENGTH: 7
<212> TYPE: PRT
<213> ORGANISM: Homo sapiens

<400> SEQUENCE: 18

Asp Asn Asn Lys Arg Pro Ser
 1               5

<210> SEQ ID NO 19
<211> LENGTH: 14
<212> TYPE: PRT
<213> ORGANISM: Homo sapiens

<400> SEQUENCE: 19

Ala Thr Trp Asp Asp Ser Leu Ser Ala Asn Ser Ala Pro Val

<210> SEQ ID NO 20
<211> LENGTH: 14
<212> TYPE: PRT
<213> ORGANISM: Homo sapiens

<400> SEQUENCE: 20

Thr Gly Thr Ser Ser Asp Val Gly Gly Tyr Asn Ala Val Ser
 1               5                  10

<210> SEQ ID NO 21
<211> LENGTH: 7
<212> TYPE: PRT
<213> ORGANISM: Homo sapiens

<400> SEQUENCE: 21

Asp Val Thr Asp Arg Pro Ser
 1               5

<210> SEQ ID NO 22
<211> LENGTH: 9
<212> TYPE: PRT
<213> ORGANISM: Homo sapiens

<400> SEQUENCE: 22

Ser Ser Tyr Gly Gly Gly Ser Asn Val
 1               5

<210> SEQ ID NO 23
<211> LENGTH: 11
<212> TYPE: PRT
<213> ORGANISM: Homo sapiens

<400> SEQUENCE: 23

Ser Gly Asp Asn Leu Gly Asp Lys Tyr Val His
 1               5                  10

<210> SEQ ID NO 24
<211> LENGTH: 7
<212> TYPE: PRT
<213> ORGANISM: Homo sapiens

<400> SEQUENCE: 24

Asp Asp Asn Lys Arg Pro Ser
 1               5

<210> SEQ ID NO 25
<211> LENGTH: 13
<212> TYPE: PRT
<213> ORGANISM: Homo sapiens

<400> SEQUENCE: 25

Gln Ala Trp Asp Ser Ser Ser Asp His Pro Gly Val Val
 1               5                  10

<210> SEQ ID NO 26
<211> LENGTH: 17
<212> TYPE: PRT
<213> ORGANISM: Mus musculus

<400> SEQUENCE: 26

Lys Ser Ser Gln Ser Leu Leu Asn Ser Gly Asn Gln Lys Asn Tyr Leu
 1               5                  10                  15

Ala

<210> SEQ ID NO 27
<211> LENGTH: 7
<212> TYPE: PRT
<213> ORGANISM: Mus musculus

<400> SEQUENCE: 27

Trp Ala Ser Thr Arg Glu Ser
 1               5

<210> SEQ ID NO 28
<211> LENGTH: 9
<212> TYPE: PRT
<213> ORGANISM: Mus musculus

<400> SEQUENCE: 28

Gln Asn Asp Tyr Ser Tyr Pro Leu Thr
 1               5

<210> SEQ ID NO 29
<211> LENGTH: 16
<212> TYPE: PRT
<213> ORGANISM: Mus musculus

<400> SEQUENCE: 29

Arg Ser Ser Gln Ser Leu Val His Ser Asn Gly Asn Thr Tyr Leu Glu
 1               5                  10                  15

<210> SEQ ID NO 30
<211> LENGTH: 7
<212> TYPE: PRT
<213> ORGANISM: Mus musculus

<400> SEQUENCE: 30

Lys Val Ser Asn Arg Phe Ser
 1               5

<210> SEQ ID NO 31
<211> LENGTH: 10
<212> TYPE: PRT
<213> ORGANISM: Mus musculus

<400> SEQUENCE: 31

Phe Gln Gly Thr His Val Pro Pro Tyr Thr
 1               5                  10

<210> SEQ ID NO 32
<211> LENGTH: 15
<212> TYPE: PRT
<213> ORGANISM: Mus musculus

<400> SEQUENCE: 32

Arg Ala Ser Glu Ser Val Asp Ser Tyr Gly Asn Ser Phe Met His
 1               5                  10                  15

<210> SEQ ID NO 33
<211> LENGTH: 7
<212> TYPE: PRT
<213> ORGANISM: Mus musculus

<400> SEQUENCE: 33

Ala Ala Ser Asn Leu Glu Ser
 1               5

```
<210> SEQ ID NO 34
<211> LENGTH: 10
<212> TYPE: PRT
<213> ORGANISM: Mus musculus

<400> SEQUENCE: 34

Gln Gln Ser Asn Glu Asp Pro Pro Trp Thr
 1               5                  10

<210> SEQ ID NO 35
<211> LENGTH: 12
<212> TYPE: PRT
<213> ORGANISM: Mus musculus

<400> SEQUENCE: 35

Ser Ala Ser Ser Ser Val Ser Ser Ser Tyr Leu His
 1               5                  10

<210> SEQ ID NO 36
<211> LENGTH: 7
<212> TYPE: PRT
<213> ORGANISM: Mus musculus

<400> SEQUENCE: 36

Arg Thr Ser Asn Leu Ala Ser
 1               5

<210> SEQ ID NO 37
<211> LENGTH: 10
<212> TYPE: PRT
<213> ORGANISM: Mus musculus

<400> SEQUENCE: 37

Gln Gln Trp Ser Ser Tyr Pro Gly Leu Thr
 1               5                  10

<210> SEQ ID NO 38
<211> LENGTH: 12
<212> TYPE: PRT
<213> ORGANISM: Mus musculus

<400> SEQUENCE: 38

Arg Ala Ser Gln Asp Asp Ile Ser Asn Tyr Leu Asn
 1               5                  10

<210> SEQ ID NO 39
<211> LENGTH: 7
<212> TYPE: PRT
<213> ORGANISM: Mus musculus

<400> SEQUENCE: 39

Tyr Ala Ser Arg Leu His Ser
 1               5

<210> SEQ ID NO 40
<211> LENGTH: 10
<212> TYPE: PRT
<213> ORGANISM: Mus musculus

<400> SEQUENCE: 40

Gln Gln Gly Asn Thr Leu Pro Pro Arg Thr
 1               5                  10

<210> SEQ ID NO 41
```

```
<211> LENGTH: 10
<212> TYPE: PRT
<213> ORGANISM: Mus musculus

<400> SEQUENCE: 41

Ser Ala Ser Ser Ser Val Ser Tyr Met His
1               5                   10

<210> SEQ ID NO 42
<211> LENGTH: 7
<212> TYPE: PRT
<213> ORGANISM: Mus musculus

<400> SEQUENCE: 42

Asp Thr Ser Lys Leu Ala Ser
1               5

<210> SEQ ID NO 43
<211> LENGTH: 12
<212> TYPE: PRT
<213> ORGANISM: Mus musculus

<400> SEQUENCE: 43

Gln Gln Trp Ser Ser Asn Pro Pro Met Pro Leu Thr
1               5                   10

<210> SEQ ID NO 44
<211> LENGTH: 5
<212> TYPE: PRT
<213> ORGANISM: Homo sapiens

<400> SEQUENCE: 44

Ser Tyr Ala Ile Ser
1               5

<210> SEQ ID NO 45
<211> LENGTH: 18
<212> TYPE: PRT
<213> ORGANISM: Homo sapiens

<400> SEQUENCE: 45

Trp Ile Asn Pro Tyr Gly Asn Gly Asp Thr Asn Tyr Ala Gln Lys Phe
1               5                   10                  15

Gln Gly

<210> SEQ ID NO 46
<211> LENGTH: 18
<212> TYPE: PRT
<213> ORGANISM: Homo sapiens

<400> SEQUENCE: 46

Ala Pro Gly Tyr Gly Ser Gly Gly Gly Cys Tyr Arg Gly Asp Tyr Phe
1               5                   10                  15

Asp Tyr

<210> SEQ ID NO 47
<211> LENGTH: 7
<212> TYPE: PRT
<213> ORGANISM: Homo sapiens

<400> SEQUENCE: 47

Ser Tyr Gly Trp Ser Trp Asn
1               5
```

<210> SEQ ID NO 48
<211> LENGTH: 19
<212> TYPE: PRT
<213> ORGANISM: Homo sapiens

<400> SEQUENCE: 48

Arg Ile Tyr Tyr Arg Ala Tyr Ser Gly Ser Thr Thr Tyr Asn Pro Ser
 1               5                  10                  15
Leu Lys Ser

<210> SEQ ID NO 49
<211> LENGTH: 19
<212> TYPE: PRT
<213> ORGANISM: Homo sapiens

<400> SEQUENCE: 49

Glu Leu Pro Gly Gly Tyr Thr Gly Asp Asp Tyr Tyr Tyr Gly Ser Gly
 1               5                  10                  15
Phe Asp Val

<210> SEQ ID NO 50
<211> LENGTH: 5
<212> TYPE: PRT
<213> ORGANISM: Homo sapiens

<400> SEQUENCE: 50

Ser Tyr Ala Met Ser
 1               5

<210> SEQ ID NO 51
<211> LENGTH: 19
<212> TYPE: PRT
<213> ORGANISM: Homo sapiens

<400> SEQUENCE: 51

Val Ile Ser Gly Lys Thr Asp Gly Gly Ser Thr Tyr Tyr Ala Asp Ser
 1               5                  10                  15
Val Lys Gly

<210> SEQ ID NO 52
<211> LENGTH: 19
<212> TYPE: PRT
<213> ORGANISM: Homo sapiens

<400> SEQUENCE: 52

Gly Arg Pro Gly Asp Ser Leu Ser Gly Tyr Tyr Tyr Tyr His Tyr
 1               5                  10                  15
Phe Asp Tyr

<210> SEQ ID NO 53
<211> LENGTH: 7
<212> TYPE: PRT
<213> ORGANISM: Mus musculus

<400> SEQUENCE: 53

Ser Gly Tyr Trp Asn Asn Ser
 1               5

<210> SEQ ID NO 54
<211> LENGTH: 17
<212> TYPE: PRT
<213> ORGANISM: Mus musculus

<400> SEQUENCE: 54

Tyr Ile Ser Gly Tyr Ser Gly Ser Thr Tyr Tyr Asn Pro Ser Leu Lys
1               5                   10                  15
Ser

<210> SEQ ID NO 55
<211> LENGTH: 18
<212> TYPE: PRT
<213> ORGANISM: Mus musculus

<400> SEQUENCE: 55

Gly Gly Tyr Gly Tyr Gly Tyr Tyr Tyr Asp Tyr Tyr Tyr Phe
1               5                   10                  15
Asp Tyr

<210> SEQ ID NO 56
<211> LENGTH: 6
<212> TYPE: PRT
<213> ORGANISM: Mus musculus

<400> SEQUENCE: 56

Asp Tyr Tyr Met Asn Asn
1               5

<210> SEQ ID NO 57
<211> LENGTH: 17
<212> TYPE: PRT
<213> ORGANISM: Mus musculus

<400> SEQUENCE: 57

Asp Ile Asn Pro Gly Asn Gly Gly Thr Ser Tyr Asn Gln Lys Phe Lys
1               5                   10                  15
Gly

<210> SEQ ID NO 58
<211> LENGTH: 16
<212> TYPE: PRT
<213> ORGANISM: Mus musculus

<400> SEQUENCE: 58

Gly Ser Tyr Tyr Ser Ser Ser Tyr Met Ala Tyr Tyr Ala Phe Asp Tyr
1               5                   10                  15

<210> SEQ ID NO 59
<211> LENGTH: 5
<212> TYPE: PRT
<213> ORGANISM: Mus musculus

<400> SEQUENCE: 59

Asp Phe Tyr Met Glu
1               5

<210> SEQ ID NO 60
<211> LENGTH: 19
<212> TYPE: PRT
<213> ORGANISM: Mus musculus

<400> SEQUENCE: 60

Ala Ser Arg Asn Lys Ala Asn Asp Tyr Thr Thr Glu Tyr Ser Ala Ser
1               5                   10                  15
Val Lys Gly

<210> SEQ ID NO 61
<211> LENGTH: 19
<212> TYPE: PRT
<213> ORGANISM: Mus musculus

<400> SEQUENCE: 61

Asp Tyr Tyr Tyr Gly Ser Ser Tyr Tyr Glu Gly Pro Val Tyr Trp Tyr
 1               5                  10                  15

Phe Asp Val

<210> SEQ ID NO 62
<211> LENGTH: 18
<212> TYPE: PRT
<213> ORGANISM: Homo sapiens

<400> SEQUENCE: 62

Pro Thr His Val Asn Val Ser Val Val Met Ala Glu Val Asp Gly Thr
 1               5                  10                  15

Cys Tyr

<210> SEQ ID NO 63
<211> LENGTH: 15
<212> TYPE: PRT
<213> ORGANISM: Mus musculus

<400> SEQUENCE: 63

Pro Thr Val Asn Val Ile Met Ser Glu Gly Asp Gly Ile Cys Tyr
 1               5                  10                  15

<210> SEQ ID NO 64
<211> LENGTH: 18
<212> TYPE: PRT
<213> ORGANISM: Mus musculus

<400> SEQUENCE: 64

Pro Thr Asn Val Ser Val Ser Val Ile Met Ser Glu Gly Asp Gly Ile
 1               5                  10                  15

Cys Tyr

<210> SEQ ID NO 65
<211> LENGTH: 18
<212> TYPE: PRT
<213> ORGANISM: Rattus norvegicus

<400> SEQUENCE: 65

Pro Thr Asn Val Asn Val Ser Val Ile Met Ser Glu Gly Asp Gly Ile
 1               5                  10                  15

Cys Tyr

<210> SEQ ID NO 66
<211> LENGTH: 18
<212> TYPE: PRT
<213> ORGANISM: Oryctolagus cuniculus

<400> SEQUENCE: 66

Pro Thr His Val Asn Val Ser Val Val Val Ala Asp Val Glu Ala Val
 1               5                  10                  15

Cys Tyr

<210> SEQ ID NO 67

<211> LENGTH: 18
<212> TYPE: PRT
<213> ORGANISM: Homo sapiens

<400> SEQUENCE: 67

Pro Thr Leu Tyr Asn Val Ser Leu Val Met Ser Asp Thr Ala Gly Thr
1               5                   10                  15

Cys Tyr

<210> SEQ ID NO 68
<211> LENGTH: 18
<212> TYPE: PRT
<213> ORGANISM: Homo sapiens

<400> SEQUENCE: 68

Pro Thr Leu Tyr Asn Val Ser Leu Ile Met Ser Asp Thr Gly Gly Thr
1               5                   10                  15

Cys Tyr

<210> SEQ ID NO 69
<211> LENGTH: 18
<212> TYPE: PRT
<213> ORGANISM: Cricetinae gen. sp.

<400> SEQUENCE: 69

Pro Thr Leu Tyr Asn Val Ser Leu Ile Met Ser Asp Ala Gly Gly Thr
1               5                   10                  15

Cys Tyr

<210> SEQ ID NO 70
<211> LENGTH: 18
<212> TYPE: PRT
<213> ORGANISM: Cricetinae gen. sp.

<400> SEQUENCE: 70

Pro Thr Leu Tyr Asn Val Ser Leu Val Leu Ser Asp Thr Ala Gly Glx
1               5                   10                  15

Cys Tyr

<210> SEQ ID NO 71
<211> LENGTH: 18
<212> TYPE: PRT
<213> ORGANISM: Rattus norvegicus

<400> SEQUENCE: 71

Pro Thr Leu Tyr Asn Val Ser Leu Ile Met Ser Asp Thr Ala Ser Thr
1               5                   10                  15

Cys Tyr

<210> SEQ ID NO 72
<211> LENGTH: 18
<212> TYPE: PRT
<213> ORGANISM: Gallus gallus

<400> SEQUENCE: 72

Pro Ser Phe Val Asn Val Ser Leu Val Leu Met Asp Thr Val Asn Ser
1               5                   10                  15

Cys Asn

<210> SEQ ID NO 73
<211> LENGTH: 19

```
<212> TYPE: PRT
<213> ORGANISM: Artificial Sequence
<220> FEATURE:
<223> OTHER INFORMATION: Description of Artificial Sequence: Signal
      sequence for plant expression vector

<400> SEQUENCE: 73

Met Asp Trp Thr Gly Arg Phe Leu Phe Val Val Ala Ala Ala Thr Gly
 1               5                  10                  15

Val Gln Ser

<210> SEQ ID NO 74
<211> LENGTH: 23
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys
            20

<210> SEQ ID NO 75
<211> LENGTH: 15
<212> TYPE: PRT
<213> ORGANISM: Homo sapiens

<400> SEQUENCE: 75

Trp Tyr Gln Gln Lys Pro Gly Lys Ala Pro Lys Leu Leu Ile Tyr
 1               5                  10                  15

<210> SEQ ID NO 76
<211> LENGTH: 32
<212> TYPE: PRT
<213> ORGANISM: Homo sapiens

<400> SEQUENCE: 76

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 77
<211> LENGTH: 10
<212> TYPE: PRT
<213> ORGANISM: Homo sapiens

<400> SEQUENCE: 77

Phe Gly Gln Gly Thr Lys Val Glu Ile Lys
 1               5                  10

<210> SEQ ID NO 78
<211> LENGTH: 23
<212> TYPE: PRT
<213> ORGANISM: Homo sapiens

<400> SEQUENCE: 78

Asp Ile Val Met Thr Gln Ser Pro Leu Ser Leu Pro Val Thr Pro Gly
 1               5                  10                  15

Glu Pro Ala Ser Ile Ser Cys
            20

<210> SEQ ID NO 79
```

-continued

```
<211> LENGTH: 15
<212> TYPE: PRT
<213> ORGANISM: Homo sapiens

<400> SEQUENCE: 79

Trp Tyr Leu Gln Lys Pro Gly Gln Ser Pro Gln Leu Leu Ile Tyr
 1               5                  10                  15

<210> SEQ ID NO 80
<211> LENGTH: 32
<212> TYPE: PRT
<213> ORGANISM: Homo sapiens

<400> SEQUENCE: 80

Gly Val Pro Asp Arg Phe Ser Gly Ser Gly Ser Gly Thr Asp Phe Thr
 1               5                  10                  15

Leu Lys Ile Ser Arg Val Glu Ala Glu Asp Val Gly Val Tyr Tyr Cys
                20                  25                  30

<210> SEQ ID NO 81
<211> LENGTH: 23
<212> TYPE: PRT
<213> ORGANISM: Homo sapiens

<400> SEQUENCE: 81

Glu Ile Val Leu Thr Gln Ser Pro Gly Thr Leu Ser Leu Ser Pro Gly
 1               5                  10                  15

Glu Arg Ala Thr Leu Ser Cys
                20

<210> SEQ ID NO 82
<211> LENGTH: 15
<212> TYPE: PRT
<213> ORGANISM: Homo sapiens

<400> SEQUENCE: 82

Trp Tyr Gln Gln Lys Pro Gly Gln Ala Pro Arg Leu Leu Ile Tyr
 1               5                  10                  15

<210> SEQ ID NO 83
<211> LENGTH: 32
<212> TYPE: PRT
<213> ORGANISM: Homo sapiens

<400> SEQUENCE: 83

Gly Ile Pro Asp Arg Phe Ser Gly Ser Gly Ser Gly Thr Asp Phe Thr
 1               5                  10                  15

Leu Thr Ile Ser Arg Leu Glu Pro Glu Asp Phe Ala Val Tyr Tyr Cys
                20                  25                  30

<210> SEQ ID NO 84
<211> LENGTH: 23
<212> TYPE: PRT
<213> ORGANISM: Homo sapiens

<400> SEQUENCE: 84

Asp Ile Val Met Thr Gln Ser Pro Asp Ser Leu Ala Val Ser Leu Gly
 1               5                  10                  15

Glu Arg Ala Thr Ile Asn Cys
                20

<210> SEQ ID NO 85
<211> LENGTH: 15
```

```
<212> TYPE: PRT
<213> ORGANISM: Homo sapiens

<400> SEQUENCE: 85

Trp Tyr Gln Gln Lys Pro Gly Gln Pro Pro Lys Leu Leu Ile Tyr
 1               5                  10                  15

<210> SEQ ID NO 86
<211> LENGTH: 32
<212> TYPE: PRT
<213> ORGANISM: Homo sapiens

<400> SEQUENCE: 86

Gly Val Pro Asp Arg Phe Ser Gly Ser Gly Ser Gly Thr Asp Phe Thr
 1               5                  10                  15

Leu Thr Ile Ser Ser Leu Gln Ala Glu Asp Val Ala Val Tyr Tyr Cys
             20                  25                  30

<210> SEQ ID NO 87
<211> LENGTH: 22
<212> TYPE: PRT
<213> ORGANISM: Homo sapiens

<400> SEQUENCE: 87

Gln Ser Val Leu Thr Gln Pro Pro Ser Val Ser Gly Ala Pro Gly Gln
 1               5                  10                  15

Arg Val Thr Ile Ser Cys
             20

<210> SEQ ID NO 88
<211> LENGTH: 15
<212> TYPE: PRT
<213> ORGANISM: Homo sapiens

<400> SEQUENCE: 88

Trp Tyr Gln Gln Leu Pro Gly Thr Ala Pro Lys Leu Leu Ile Tyr
 1               5                  10                  15

<210> SEQ ID NO 89
<211> LENGTH: 32
<212> TYPE: PRT
<213> ORGANISM: Homo sapiens

<400> SEQUENCE: 89

Gly Val Pro Asp Arg Phe Ser Gly Ser Lys Ser Gly Thr Ser Ala Ser
 1               5                  10                  15

Leu Ala Ile Asn Gly Leu Gln Ser Glu Asp Glu Ala Asp Tyr Tyr Cys
             20                  25                  30

<210> SEQ ID NO 90
<211> LENGTH: 11
<212> TYPE: PRT
<213> ORGANISM: Homo sapiens

<400> SEQUENCE: 90

Phe Gly Gly Gly Thr Lys Leu Thr Val Leu Gly
 1               5                  10

<210> SEQ ID NO 91
<211> LENGTH: 22
<212> TYPE: PRT
<213> ORGANISM: Homo sapiens

<400> SEQUENCE: 91
```

```
Gln Ser Ala Leu Thr Gln Pro Ala Ser Val Ser Gly Ser Pro Gly Gln
  1               5                  10                  15

Ser Ile Thr Ile Ser Cys
                20
```

<210> SEQ ID NO 92
<211> LENGTH: 15
<212> TYPE: PRT
<213> ORGANISM: Homo sapiens

<400> SEQUENCE: 92

```
Trp Tyr Gln Gln His Pro Gly Lys Ala Pro Lys Leu Leu Ile Tyr
  1               5                  10                  15
```

<210> SEQ ID NO 93
<211> LENGTH: 32
<212> TYPE: PRT
<213> ORGANISM: Homo sapiens

<400> SEQUENCE: 93

```
Gly Val Pro Asp Arg Phe Ser Gly Ser Lys Ser Gly Asn Thr Ala Ser
  1               5                  10                  15

Leu Thr Ile Ser Gly Leu Gln Ala Glu Asp Glu Ala Asp Tyr Tyr Cys
                20                  25                  30
```

<210> SEQ ID NO 94
<211> LENGTH: 11
<212> TYPE: PRT
<213> ORGANISM: Homo sapiens

<400> SEQUENCE: 94

```
Phe Gly Gly Gly Thr Lys Val Thr Val Leu Gly
  1               5                  10
```

<210> SEQ ID NO 95
<211> LENGTH: 22
<212> TYPE: PRT
<213> ORGANISM: Homo sapiens

<400> SEQUENCE: 95

```
Ser Tyr Glu Leu Thr Gln Pro Pro Ser Val Ser Val Ser Pro Gly Gln
  1               5                  10                  15

Thr Ala Arg Ile Thr Cys
                20
```

<210> SEQ ID NO 96
<211> LENGTH: 15
<212> TYPE: PRT
<213> ORGANISM: Homo sapiens

<400> SEQUENCE: 96

```
Trp Tyr Gln Gln Lys Pro Gly Gln Ala Pro Val Leu Val Ile Tyr
  1               5                  10                  15
```

<210> SEQ ID NO 97
<211> LENGTH: 32
<212> TYPE: PRT
<213> ORGANISM: Homo sapiens

<400> SEQUENCE: 97

```
Gly Ile Pro Glu Arg Phe Ser Gly Ser Asn Ser Gly Asn Thr Ala Thr
  1               5                  10                  15
```

-continued

Leu Thr Ile Ser Gly Val Gln Ala Gly Asp Glu Ala Asp Tyr Tyr Cys
            20                  25                  30

<210> SEQ ID NO 98
<211> LENGTH: 21
<212> TYPE: PRT
<213> ORGANISM: Homo sapiens

<400> SEQUENCE: 98

Ser Glu Leu Thr Gln Pro Pro Ser Val Ser Val Ala Leu Gly Gln Thr
1               5                   10                  15

Val Arg Ile Thr Cys
            20

<210> SEQ ID NO 99
<211> LENGTH: 15
<212> TYPE: PRT
<213> ORGANISM: Homo sapiens

<400> SEQUENCE: 99

Trp Tyr Gln Gln Lys Pro Gly Gln Ala Pro Leu Leu Val Ile Tyr
1               5                   10                  15

<210> SEQ ID NO 100
<211> LENGTH: 32
<212> TYPE: PRT
<213> ORGANISM: Homo sapiens

<400> SEQUENCE: 100

Gly Ile Pro Asp Arg Phe Ser Gly Ser Ser Ser Gly His Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 101
<211> LENGTH: 21
<212> TYPE: PRT
<213> ORGANISM: Homo sapiens

<400> SEQUENCE: 101

Ser Ala Leu Thr Gln Pro Pro Ser Ala Ser Gly Ser Leu Gly Gln Ser
1               5                   10                  15

Val Thr Ile Ser Cys
            20

<210> SEQ ID NO 102
<211> LENGTH: 15
<212> TYPE: PRT
<213> ORGANISM: Homo sapiens

<400> SEQUENCE: 102

Trp Tyr Gln Gln His Pro Gly Arg Ala Pro Lys Leu Val Ile Phe
1               5                   10                  15

<210> SEQ ID NO 103
<211> LENGTH: 32
<212> TYPE: PRT
<213> ORGANISM: Homo sapiens

<400> SEQUENCE: 103

Gly Val Pro Asp Arg Phe Ser Gly Ser Lys Ser Asp Gln Thr Ala Ser
1               5                   10                  15

Leu Thr Val Ser Gly Leu Arg Ala Glu Asp Glu Ala Asp Tyr Tyr Cys

<210> SEQ ID NO 104
<211> LENGTH: 11
<212> TYPE: PRT
<213> ORGANISM: Homo sapiens

<400> SEQUENCE: 104

Phe Gly Gly Gly Thr Lys Leu Thr Val Leu Arg
 1               5                  10

<210> SEQ ID NO 105
<211> LENGTH: 22
<212> TYPE: PRT
<213> ORGANISM: Homo sapiens

<400> SEQUENCE: 105

Asn Phe Met Leu Thr Gln Pro His Ser Val Ser Glu Ser Pro Gly Lys
 1               5                  10                  15

Thr Val Thr Ile Ser Cys
            20

<210> SEQ ID NO 106
<211> LENGTH: 15
<212> TYPE: PRT
<213> ORGANISM: Homo sapiens

<400> SEQUENCE: 106

Trp Tyr Gln Gln Arg Pro Gly Ser Ala Pro Thr Thr Val Ile Tyr
 1               5                  10                  15

<210> SEQ ID NO 107
<211> LENGTH: 31
<212> TYPE: PRT
<213> ORGANISM: Homo sapiens

<400> SEQUENCE: 107

Gly Val Pro Asp Arg Phe Ser Gly Ser Ser Asn Ser Ala Ser Leu
 1               5                  10                  15

Thr Ile Ser Gly Leu Lys Thr Glu Asp Glu Ala Asp Tyr Tyr Cys
            20                  25                  30

<210> SEQ ID NO 108
<211> LENGTH: 23
<212> TYPE: PRT
<213> ORGANISM: Mus musculus

<400> SEQUENCE: 108

Asp Ile Val Met Thr Gln Ser Pro Ser Ser Leu Ala Val Ser Ala Gly
 1               5                  10                  15

Glu Lys Val Thr Met Ser Cys
            20

<210> SEQ ID NO 109
<211> LENGTH: 15
<212> TYPE: PRT
<213> ORGANISM: Mus musculus

<400> SEQUENCE: 109

Trp Tyr Gln Gln Lys Pro Gly Gln Ser Pro Lys Leu Leu Ile Tyr
 1               5                  10                  15

<210> SEQ ID NO 110

```
<211> LENGTH: 32
<212> TYPE: PRT
<213> ORGANISM: Mus musculus

<400> SEQUENCE: 110

Gly Val Pro Asp Arg Phe Thr Gly Ser Gly Ser Gly Thr Asp Phe Thr
  1               5                  10                  15
Leu Thr Ile Ser Ser Val Gln Ala Glu Asp Leu Ala Val Tyr Tyr Cys
             20                  25                  30

<210> SEQ ID NO 111
<211> LENGTH: 10
<212> TYPE: PRT
<213> ORGANISM: Mus musculus

<400> SEQUENCE: 111

Phe Gly Ala Gly Thr Lys Leu Glu Leu Lys
  1               5                  10

<210> SEQ ID NO 112
<211> LENGTH: 23
<212> TYPE: PRT
<213> ORGANISM: Mus musculus

<400> SEQUENCE: 112

Asp Val Val Met Thr Gln Thr Pro Leu Ser Leu Pro Val Ser Leu Gly
  1               5                  10                  15
Asp Gln Ala Ser Ile Ser Cys
             20

<210> SEQ ID NO 113
<211> LENGTH: 15
<212> TYPE: PRT
<213> ORGANISM: Mus musculus

<400> SEQUENCE: 113

Trp Tyr Leu Gln Lys Pro Gly Gln Ser Pro Lys Leu Leu Ile Tyr
  1               5                  10                  15

<210> SEQ ID NO 114
<211> LENGTH: 32
<212> TYPE: PRT
<213> ORGANISM: Mus musculus

<400> SEQUENCE: 114

Gly Val Pro Asp Arg Phe Ser Gly Ser Gly Ser Gly Thr Asp Phe Thr
  1               5                  10                  15
Leu Lys Ile Ser Arg Val Glu Ala Glu Asp Leu Gly Val Tyr Tyr Cys
             20                  25                  30

<210> SEQ ID NO 115
<211> LENGTH: 10
<212> TYPE: PRT
<213> ORGANISM: Mus musculus

<400> SEQUENCE: 115

Phe Gly Gly Gly Thr Lys Leu Glu Ile Lys
  1               5                  10

<210> SEQ ID NO 116
<211> LENGTH: 23
<212> TYPE: PRT
<213> ORGANISM: Mus musculus
```

```
<400> SEQUENCE: 116

Asp Ile Val Leu Thr Gln Ser Pro Ala Ser Leu Ala Val Ser Leu Gly
 1               5                  10                  15

Gln Arg Ala Thr Ile Ser Cys
            20

<210> SEQ ID NO 117
<211> LENGTH: 15
<212> TYPE: PRT
<213> ORGANISM: Mus musculus

<400> SEQUENCE: 117

Trp Tyr Gln Gln Lys Pro Gly Gln Pro Pro Lys Leu Leu Ile Tyr
 1               5                  10                  15

<210> SEQ ID NO 118
<211> LENGTH: 32
<212> TYPE: PRT
<213> ORGANISM: Mus musculus

<400> SEQUENCE: 118

Gly Val Pro Ala Arg Phe Ser Gly Ser Gly Ser Gly Thr Asp Phe Thr
 1               5                  10                  15

Leu Asn Ile His Pro Val Glu Glu Asp Ala Ala Thr Tyr Tyr Cys
            20                  25                  30

<210> SEQ ID NO 119
<211> LENGTH: 23
<212> TYPE: PRT
<213> ORGANISM: Mus musculus

<400> SEQUENCE: 119

Glu Ile Val Leu Thr Gln Ser Pro Ala Ile Met Ser Ala Ser Pro Gly
 1               5                  10                  15

Glu Lys Val Thr Met Thr Cys
            20

<210> SEQ ID NO 120
<211> LENGTH: 15
<212> TYPE: PRT
<213> ORGANISM: Mus musculus

<400> SEQUENCE: 120

Trp Tyr Gln Gln Lys Pro Gly Asn Ser Pro Lys Leu Trp Ile Tyr
 1               5                  10                  15

<210> SEQ ID NO 121
<211> LENGTH: 32
<212> TYPE: PRT
<213> ORGANISM: Mus musculus

<400> SEQUENCE: 121

Gly Val Pro Ala Arg Phe Ser Gly Ser Gly Ser Gly Thr Ser Tyr Ser
 1               5                  10                  15

Leu Thr Ile Ser Ser Met Glu Ala Glu Asp Ala Ala Thr Tyr Tyr Cys
            20                  25                  30

<210> SEQ ID NO 122
<211> LENGTH: 10
<212> TYPE: PRT
<213> ORGANISM: Mus musculus

<400> SEQUENCE: 122
```

```
Phe Gly Ala Gly Thr Lys Leu Glu Ile Lys
  1               5                  10

<210> SEQ ID NO 123
<211> LENGTH: 23
<212> TYPE: PRT
<213> ORGANISM: Mus musculus

<400> SEQUENCE: 123

Asp Ile Gln Met Thr Gln Ser Pro Ser Ser Leu Ser Ala Ser Leu Gly
  1               5                  10                  15

Asp Arg Val Thr Ile Thr Cys
             20

<210> SEQ ID NO 124
<211> LENGTH: 15
<212> TYPE: PRT
<213> ORGANISM: Mus musculus

<400> SEQUENCE: 124

Trp Tyr Gln Gln Lys Pro Gly Gly Ser Pro Lys Leu Leu Ile Tyr
  1               5                  10                  15

<210> SEQ ID NO 125
<211> LENGTH: 32
<212> TYPE: PRT
<213> ORGANISM: Mus musculus

<400> SEQUENCE: 125

Gly Val Pro Ser Arg Phe Ser Gly Ser Gly Ser Gly Thr Asp Tyr Ser
  1               5                  10                  15

Leu Thr Ile Ser Gln Leu Glu Gln Glu Asp Ile Ala Thr Tyr Phe Cys
             20                  25                  30

<210> SEQ ID NO 126
<211> LENGTH: 23
<212> TYPE: PRT
<213> ORGANISM: Mus musculus

<400> SEQUENCE: 126

Gln Ile Val Leu Thr Gln Ser Pro Ala Ile Met Ser Ala Ser Pro Gly
  1               5                  10                  15

Glu Lys Val Thr Met Thr Cys
             20

<210> SEQ ID NO 127
<211> LENGTH: 15
<212> TYPE: PRT
<213> ORGANISM: Mus musculus

<400> SEQUENCE: 127

Trp Tyr Gln Gln Lys Ser Gly Thr Ser Pro Lys Arg Trp Ile Tyr
  1               5                  10                  15

<210> SEQ ID NO 128
<211> LENGTH: 32
<212> TYPE: PRT
<213> ORGANISM: Mus musculus

<400> SEQUENCE: 128

Gly Val Pro Ala Arg Phe Ser Gly Ser Gly Ser Gly Thr Ser Tyr Ser
  1               5                  10                  15
```

Leu Thr Ile Ser Ser Met Glu Ala Glu Asp Ala Ala Thr Tyr Tyr Cys
            20                  25                  30

<210> SEQ ID NO 129
<211> LENGTH: 22
<212> TYPE: PRT
<213> ORGANISM: Mus musculus

<400> SEQUENCE: 129

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 130
<211> LENGTH: 15
<212> TYPE: PRT
<213> ORGANISM: Mus musculus

<400> SEQUENCE: 130

Trp Val Gln Glu Lys Pro Asp His Leu Phe Thr Gly Leu Ile Gly
1               5                   10                  15

<210> SEQ ID NO 131
<211> LENGTH: 32
<212> TYPE: PRT
<213> ORGANISM: Mus musculus

<400> SEQUENCE: 131

Gly Val Pro Ala Arg Phe Ser Gly Ser Leu Ile Gly Asp Lys Ala Ala
1               5                   10                  15

Leu Thr Ile Thr Gly Ala Gln Thr Glu Asp Glu Ala Ile Tyr Phe Cys
            20                  25                  30

<210> SEQ ID NO 132
<211> LENGTH: 11
<212> TYPE: PRT
<213> ORGANISM: Mus musculus

<400> SEQUENCE: 132

Phe Gly Gly Gly Thr Lys Leu Thr Val Leu Gly
1               5                   10

<210> SEQ ID NO 133
<211> LENGTH: 30
<212> TYPE: PRT
<213> ORGANISM: Homo sapiens

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 134
<211> LENGTH: 14
<212> TYPE: PRT
<213> ORGANISM: Homo sapiens

<400> SEQUENCE: 134

Trp Val Arg Gly Ala Pro Gly Gln Gly Leu Glu Trp Met Gly
1               5                   10

<210> SEQ ID NO 135
<211> LENGTH: 32
<212> TYPE: PRT
<213> ORGANISM: Homo sapiens

<400> SEQUENCE: 135

Arg Val Thr Ile Thr Ala Asp Thr Ser Thr Ser Thr Ala Tyr Met Glu
 1               5                  10                  15

Leu Ser Ser Leu Arg Ser Glu Asp Thr Ala Val Tyr Tyr Cys Ala Arg
            20                  25                  30

<210> SEQ ID NO 136
<211> LENGTH: 11
<212> TYPE: PRT
<213> ORGANISM: Homo sapiens

<400> SEQUENCE: 136

Trp Gly Gln Gly Thr Leu Val Thr Val Ser Ser
 1               5                  10

<210> SEQ ID NO 137
<211> LENGTH: 30
<212> TYPE: PRT
<213> ORGANISM: Homo sapiens

<400> SEQUENCE: 137

Gln Val Gln Leu Gln Glu Ser Gly Pro Gly Leu Val Lys Pro Ser Gln
 1               5                  10                  15

Thr Leu Ser Leu Thr Cys Thr Val Ser Gly Ser Val Ser
            20                  25                  30

<210> SEQ ID NO 138
<211> LENGTH: 14
<212> TYPE: PRT
<213> ORGANISM: Homo sapiens

<400> SEQUENCE: 138

Trp Ile Arg Gln Pro Pro Gly Lys Gly Leu Glu Trp Ile Gly
 1               5                  10

<210> SEQ ID NO 139
<211> LENGTH: 32
<212> TYPE: PRT
<213> ORGANISM: Homo sapiens

<400> SEQUENCE: 139

Arg Val Thr Ile Ser Val Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
            20                  25                  30

<210> SEQ ID NO 140
<211> LENGTH: 30
<212> TYPE: PRT
<213> ORGANISM: Homo sapiens

<400> SEQUENCE: 140

Glu Val Gln Leu Val Glu Ser Gly Gly Gly Leu Val Gln Pro Gly Gly
 1               5                  10                  15

Ser Leu Arg Leu Ser Cys Ala Ala Cys Gly Phe Thr Phe Ser
            20                  25                  30

<210> SEQ ID NO 141

<211> LENGTH: 14
<212> TYPE: PRT
<213> ORGANISM: Homo sapiens

<400> SEQUENCE: 141

Trp Val Arg Gln Ala Pro Gly Lys Gly Leu Glu Trp Val Ser
 1               5                  10

<210> SEQ ID NO 142
<211> LENGTH: 32
<212> TYPE: PRT
<213> ORGANISM: Homo sapiens

<400> SEQUENCE: 142

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
                20                  25                  30

<210> SEQ ID NO 143
<211> LENGTH: 30
<212> TYPE: PRT
<213> ORGANISM: Mus musculus

<400> SEQUENCE: 143

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr
                20                  25                  30

<210> SEQ ID NO 144
<211> LENGTH: 14
<212> TYPE: PRT
<213> ORGANISM: Mus musculus

<400> SEQUENCE: 144

Trp Ile Arg Gln Phe Pro Gly Asn Lys Leu Glu Trp Met Gly
 1               5                  10

<210> SEQ ID NO 145
<211> LENGTH: 32
<212> TYPE: PRT
<213> ORGANISM: Mus musculus

<400> SEQUENCE: 145

Arg Ile Ser Ile Thr Arg Asp Thr Ser Lys Asn Gln Tyr Phe Leu Gln
 1               5                  10                  15

Leu Asn Ser Val Thr Thr Glu Asp Thr Ala Thr Tyr Tyr Cys Ala Arg
                20                  25                  30

<210> SEQ ID NO 146
<211> LENGTH: 11
<212> TYPE: PRT
<213> ORGANISM: Mus musculus

<400> SEQUENCE: 146

Trp Gly Gln Gly Thr Thr Val Thr Val Ser Ser
 1               5                  10

<210> SEQ ID NO 147
<211> LENGTH: 30
<212> TYPE: PRT
<213> ORGANISM: Mus musculus

```
<400> SEQUENCE: 147

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr
            20                  25                  30

<210> SEQ ID NO 148
<211> LENGTH: 14
<212> TYPE: PRT
<213> ORGANISM: Mus musculus

<400> SEQUENCE: 148

Trp Val Arg Gln Pro Pro Gly Lys Gly Leu Glu Trp Leu Gly
 1               5                  10

<210> SEQ ID NO 149
<211> LENGTH: 32
<212> TYPE: PRT
<213> ORGANISM: Mus musculus

<400> SEQUENCE: 149

Arg Leu Ser Ile Ser Lys Asp Gln Ser Lys Ser Gln Val Phe Leu Lys
 1               5                  10                  15

Met Asn Ser Leu Gln Thr Asp Asp Thr Ala Met Tyr Tyr Cys Ala Arg
            20                  25                  30

<210> SEQ ID NO 150
<211> LENGTH: 11
<212> TYPE: PRT
<213> ORGANISM: Mus musculus

<400> SEQUENCE: 150

Trp Gly Gln Gly Thr Ser Val Thr Val Ser Ser
 1               5                  10

<210> SEQ ID NO 151
<211> LENGTH: 30
<212> TYPE: PRT
<213> ORGANISM: Mus musculus

<400> SEQUENCE: 151

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr
            20                  25                  30

<210> SEQ ID NO 152
<211> LENGTH: 14
<212> TYPE: PRT
<213> ORGANISM: Mus musculus

<400> SEQUENCE: 152

Trp Val Lys Gln Ser Pro Gly Lys Ser Leu Glu Trp Ile Gly
 1               5                  10

<210> SEQ ID NO 153
<211> LENGTH: 32
<212> TYPE: PRT
<213> ORGANISM: Mus musculus

<400> SEQUENCE: 153

Lys Ala Thr Leu Thr Val Asp Lys Ser Ser Ser Thr Ala Tyr Met Gln
 1               5                  10                  15
```

Leu Ser Ser Leu Thr Ser Glu Asp Ser Ala Val Tyr Tyr Cys Ala Arg
            20                  25                  30

<210> SEQ ID NO 154
<211> LENGTH: 30
<212> TYPE: PRT
<213> ORGANISM: Mus musculus

<400> SEQUENCE: 154

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Pro Thr
            20                  25                  30

<210> SEQ ID NO 155
<211> LENGTH: 14
<212> TYPE: PRT
<213> ORGANISM: Mus musculus

<400> SEQUENCE: 155

Trp Val Lys Gln Arg Pro Gly Gln Gly Leu Glu Trp Ile Gly
 1               5                  10

<210> SEQ ID NO 156
<211> LENGTH: 32
<212> TYPE: PRT
<213> ORGANISM: Mus musculus

<400> SEQUENCE: 156

Lys Ala Thr Leu Thr Val Asp Lys Ser Ser Thr Ala Tyr Met Gln
 1               5                  10                  15

Leu Ser Ser Leu Thr Ser Glu Asp Ser Ala Val Tyr Tyr Cys Ala Arg
            20                  25                  30

<210> SEQ ID NO 157
<211> LENGTH: 11
<212> TYPE: PRT
<213> ORGANISM: Mus musculus

<400> SEQUENCE: 157

Trp Val Gln Gly Thr Thr Val Thr Val Ser Ser
 1               5                  10

<210> SEQ ID NO 158
<211> LENGTH: 30
<212> TYPE: PRT
<213> ORGANISM: Mus musculus

<400> SEQUENCE: 158

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys
            20                  25                  30

<210> SEQ ID NO 159
<211> LENGTH: 14
<212> TYPE: PRT
<213> ORGANISM: Mus musculus

<400> SEQUENCE: 159

Trp Val Lys Gln Arg Pro Glu Gln Gly Leu Glu Trp Ile Gly
 1               5                  10

```
<210> SEQ ID NO 160
<211> LENGTH: 32
<212> TYPE: PRT
<213> ORGANISM: Mus musculus

<400> SEQUENCE: 160

Lys Ala Thr Ile Thr Ala Asp Thr Ser Ser Asn Thr Ala Tyr Leu Gln
  1               5                  10                  15

Leu Ser Ser Leu Thr Ser Glu Asp Thr Ala Val Tyr Tyr Cys Ala Arg
                 20                  25                  30

<210> SEQ ID NO 161
<211> LENGTH: 11
<212> TYPE: PRT
<213> ORGANISM: Mus musculus

<400> SEQUENCE: 161

Trp Gly Gln Gly Thr Leu Val Thr Val Ser Ser
  1               5                  10

<210> SEQ ID NO 162
<211> LENGTH: 30
<212> TYPE: PRT
<213> ORGANISM: Mus musculus

<400> SEQUENCE: 162

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Ser
                 20                  25                  30

<210> SEQ ID NO 163
<211> LENGTH: 14
<212> TYPE: PRT
<213> ORGANISM: Mus musculus

<400> SEQUENCE: 163

Trp Val Arg Gln Pro Pro Gly Lys Ala Leu Glu Trp Ile Ala
  1               5                  10

<210> SEQ ID NO 164
<211> LENGTH: 32
<212> TYPE: PRT
<213> ORGANISM: Mus musculus

<400> SEQUENCE: 164

Arg Phe Thr Val Ser Arg Asp Thr Ser Gln Ser Ile Ile Tyr Leu Gln
  1               5                  10                  15

Met Asn Ala Leu Arg Ala Glu Asp Thr Ala Ile Tyr Tyr Cys Ala Arg
                 20                  25                  30

<210> SEQ ID NO 165
<211> LENGTH: 11
<212> TYPE: PRT
<213> ORGANISM: Mus musculus

<400> SEQUENCE: 165

Trp Gly Ala Gly Thr Thr Val Thr Val Ser Ser
  1               5                  10

<210> SEQ ID NO 166
<211> LENGTH: 30
<212> TYPE: PRT
```

<213> ORGANISM: Mus musculus

<400> SEQUENCE: 166

Glu Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser
            20                  25                  30

<210> SEQ ID NO 167
<211> LENGTH: 14
<212> TYPE: PRT
<213> ORGANISM: Mus musculus

<400> SEQUENCE: 167

Trp Val Arg Gln Ala Pro Gly Lys Gly Leu Glu Trp Ile Gly
 1               5                  10

<210> SEQ ID NO 168
<211> LENGTH: 32
<212> TYPE: PRT
<213> ORGANISM: Mus musculus

<400> SEQUENCE: 168

Lys Phe Ile Ile Ser Arg Asp Gln Ala Lys Gln Thr Leu Tyr Leu Gln
 1               5                  10                  15

Met Ser Lys Val Arg Ser Glu Asp Thr Ala Leu Tyr Tyr Cys Ala Arg
            20                  25                  30

<210> SEQ ID NO 169
<211> LENGTH: 11
<212> TYPE: PRT
<213> ORGANISM: Mus musculus

<400> SEQUENCE: 169

Trp Gly Gln Gly Thr Thr Val Thr Val Ser Ser
 1               5                  10

<210> SEQ ID NO 170
<211> LENGTH: 30
<212> TYPE: PRT
<213> ORGANISM: Mus musculus

<400> SEQUENCE: 170

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser
            20                  25                  30

<210> SEQ ID NO 171
<211> LENGTH: 14
<212> TYPE: PRT
<213> ORGANISM: Mus musculus

<400> SEQUENCE: 171

Trp Val Arg Gln Ser Pro Glu Lys Gly Leu Glu Trp Val Ala
 1               5                  10

<210> SEQ ID NO 172
<211> LENGTH: 32
<212> TYPE: PRT
<213> ORGANISM: Mus musculus

<400> SEQUENCE: 172

Arg Phe Thr Ile Ser Arg Asp Asp Ser Lys Ser Ser Val Tyr Leu Gln
1               5                   10                  15

Met Asn Asn Leu Arg Ala Glu Asp Thr Gly Ile Tyr Tyr Cys Thr Thr
                20                  25                  30

<210> SEQ ID NO 173
<211> LENGTH: 30
<212> TYPE: PRT
<213> ORGANISM: Mus musculus

<400> SEQUENCE: 173

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser
                20                  25                  30

<210> SEQ ID NO 174
<211> LENGTH: 14
<212> TYPE: PRT
<213> ORGANISM: Mus musculus

<400> SEQUENCE: 174

Trp Val Arg Gln Thr Pro Glu Lys Arg Leu Glu Trp Val Ala
1               5                   10

<210> SEQ ID NO 175
<211> LENGTH: 32
<212> TYPE: PRT
<213> ORGANISM: Mus musculus

<400> SEQUENCE: 175

Arg Phe Thr Ile Ser Arg Asp Gln Ala Lys Gln Thr Leu Tyr Leu Gln
1               5                   10                  15

Met Ser Ser Leu Arg Ser Glu Asp Thr Ala Met Tyr Tyr Cys Ala Arg
                20                  25                  30

<210> SEQ ID NO 176
<211> LENGTH: 30
<212> TYPE: PRT
<213> ORGANISM: Mus musculus

<400> SEQUENCE: 176

Glu Val Gln Leu Gln Gln Ser Gly Ala Glu Leu Val Arg Ala Gly Ser
1               5                   10                  15

Ser Val Lys Met Ser Cys Lys Ala Ser Gly Tyr Thr Phe Thr
                20                  25                  30

<210> SEQ ID NO 177
<211> LENGTH: 14
<212> TYPE: PRT
<213> ORGANISM: Mus musculus

<400> SEQUENCE: 177

Trp Val Lys Gln Arg Pro Gly Gln Gly Leu Glu Trp Ile Gly
1               5                   10

<210> SEQ ID NO 178
<211> LENGTH: 32
<212> TYPE: PRT
<213> ORGANISM: Mus musculus

<400> SEQUENCE: 178

Lys Thr Thr Leu Thr Val Asp Lys Ser Ser Ser Thr Ala Tyr Met Gln

-continued

```
  1               5                   10                  15

Leu Arg Ser Leu Thr Ser Glu Asp Ser Ala Val Tyr Phe Cys Ala Arg
             20                  25                  30

<210> SEQ ID NO 179
<211> LENGTH: 11
<212> TYPE: PRT
<213> ORGANISM: Mus musculus

<400> SEQUENCE: 179

Trp Gly Gln Gly Thr Thr Leu Thr Val Ser Ser
  1               5                   10

<210> SEQ ID NO 180
<211> LENGTH: 31
<212> TYPE: PRT
<213> ORGANISM: Mus musculus

<400> SEQUENCE: 180

Ser Glu Val Gln Leu Val Glu Ser Gly Gly Gly Leu Val Lys Pro Gly
  1               5                   10                  15

Gly Ser Val Lys Leu Ser Cys Lys Ala Ser Gly Phe Thr Phe Ser
             20                  25                  30

<210> SEQ ID NO 181
<211> LENGTH: 14
<212> TYPE: PRT
<213> ORGANISM: Mus musculus

<400> SEQUENCE: 181

Trp Val Arg Gln Ala Pro Gly Lys Gly Leu Glu Trp Val Gly
  1               5                   10

<210> SEQ ID NO 182
<211> LENGTH: 32
<212> TYPE: PRT
<213> ORGANISM: Mus musculus

<400> SEQUENCE: 182

Arg Phe Thr Ile Ser Arg Asp Asn Ser Lys Ser Thr Leu Tyr Leu Gln
  1               5                   10                  15

Met Ser Ser Leu Arg Ser Glu Asp Thr Ala Thr Tyr Tyr Cys Ala Arg
             20                  25                  30
```